Figure 2:
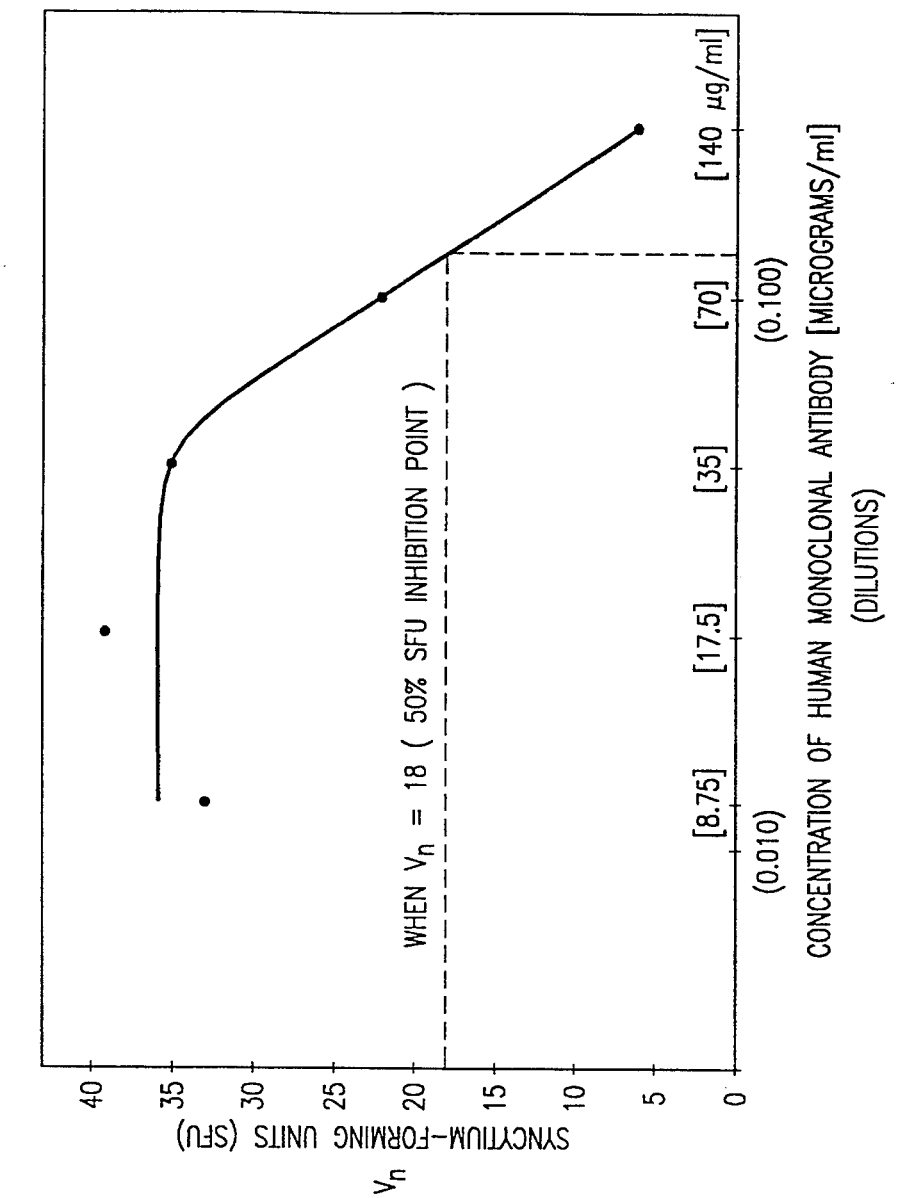

United States Patent [19]

Cotropia

[11] Patent Number: 5,459,060
[45] Date of Patent: Oct. 17, 1995

[54] HUMAN MONOCLONAL ANTIBODIES DIRECTED AGAINST THE TRANSMEMBRANE GLYCOPROTEIN (GP41) OF HUMAN IMMUNODEFICIENCY VIRUS-1 (HIV-1)

[75] Inventor: Joseph P. Cotropia, Philadelphia, Pa.

[73] Assignee: Bioclonetics Incorporated, Philadelphia, Pa.

[21] Appl. No.: 633,964

[22] Filed: Dec. 26, 1990

Related U.S. Application Data

[63] Continuation-in-part of Ser. No. 396,751, Aug. 24, 1989.

[51] Int. Cl.$^6$ ............................ C12N 5/24; C07K 15/28; A61K 39/42
[52] U.S. Cl. .................... 435/240.27; 435/70.21; 435/172.2; 530/388.15; 530/388.35; 424/142.1; 424/148.1
[58] Field of Search .................... 424/85.8, 85.91, 424/86, 89, 142.1, 148.1, 160.1, 188.1, 208.1; 435/70.21, 172.2, 240.27; 530/388.15, 388.35, 387.9, 389.4, 391.7; 935/99, 100, 107, 108

[56] References Cited

U.S. PATENT DOCUMENTS

| | | | |
|---|---|---|---|
| 4,722,888 | 2/1988 | Broder et al. | 435/5 |
| 4,755,457 | 7/1988 | Robert-Guroff et al. | 435/5 |
| 4,798,797 | 1/1989 | Montagnier et al. | 435/235 |
| 4,812,556 | 3/1989 | Vahlne et al. | 530/324 |
| 4,833,071 | 5/1989 | Wang et al. | 435/5 |
| 4,833,072 | 5/1989 | Krchnak et al. | 435/5 |
| 4,839,288 | 6/1989 | Montagnier et al. | 435/235 |
| 5,087,557 | 2/1992 | McClure | 435/5 |

FOREIGN PATENT DOCUMENTS

| | | |
|---|---|---|
| 0316495 | 5/1989 | European Pat. Off. . |
| 9015071 | 12/1990 | WIPO . |

OTHER PUBLICATIONS

Fahey et al., "Status of Immune-based Therapies in HIV Infections and AIDS", *Clin. Exp. Immunol.* 88:1–5, 1992.

Fox, J. L., "No Winners Against AIDS," *Bio/Technology* 12:128, Feb. 1994.

Altman, L. K., "AIDS Study Casts Doubt on Value of Hastened Drug Approval in U.S.", *New York Times*, Apr. 6, 1993.

Fitzer-Schiller, G., "Centocor Stops Trials of Flagship Drug," *Washington Post*, Jan. 19, 1993.

Shafferman et al., "Patterns of Antibody Recognition of Selected Conserved Amino Acid Sequences from the HIV Envelope in Sera from Different Stages of HIV Infection:", *AIDS Research and Human Retroviruses* (1989) 5:33–39.

Lambert et al., Abstract No. W.C.O.11 "Inhibitors of HIV–1 Protease Inhibit the Processing of GAG and GAG/POL Polyproteins in Infected T-Cells", V. International Conference on AIDS (1989), p. 526.

Emini et al., Abstract No. Th.C.O.30 "Neutralization of In Vivo HIV–1 Infectivity Mediated by In Vitro Neutralizing Antibody" V. International Conference on AIDS (1989), p. 538.

Gorny et al., "General of human monoclonal antibodies to human immunodeficiency virus", *Proceedings of the National Academy of Science* (U.S.A.) (1989) 86:1624–1628.

Kawamura et al., Abstract No. Th.C.O.4, "A Hybridoma Producing Human Monoclonal IgG Neutralizes the HTLVIIIb Isolate In Vitro", V. International Conference on AIDS, p. 533.

Boyer et al., Abstract No. T.C.P.59, "Characterization of Human Monoclonal Antibodies Against HIV–1 with Group Specific Neutralizing Activities", V. International Conference on AIDS (1989), p. 576.

Zolla–Pazner et al., Abstract No. Th.C.O.10, "Biological Functions of Human Monoclonal Antibodies to HIV", V. International Conference on AIDS (1989), p. 534.

Pinter et al., "Oligomeric Structure of gp41, the Transmembrane Protein of Human Immunodeficiency Virus Type 1" *Journal of Virology* (1989) 63:2674–2679.

Till et al., "Human immunodeficiency virus-infected T-cells and monocytes are killed by monoclonal human anti-gp41 antibodies coupled to ricin A chain", Proceedings of the National Academy of Science (U.S.A.) (1989) 86:1987–1991.

Navia et al., Abstract No. M.C.O.23 "Three-dimensional Structure of the HIV–1 Protease and its Role in Virus Maturation", V. International Conference on AIDS (1989), p. 513.

Debouck et al., Abstract No. T.C.O.11 "Expression, Purification, Structure, Activity and Substrate Specificity of the HIV–1 Retroviral Protease", V. International Conference on AIDS (1989), p. 517.

Tyler et al., Abstract No. T.C.O.33 "Identification of Sites within gp41 which Serve as Targets for ADCC Using Human Monoclonal Antibodies", V. International Conference on AIDS (1989), p. 521.

Anthony S. Fauci, "The Human Immunodeficiency Virus: Infectivity and Mechanisms of Pathogenesis", *Science* (1988) 239:617–622.

Gallo et al., "AIDS in 1988", *Scientific American* (1988) 259:41–48.

Robert–Guroff et al., "Spectrum of HIV–1 Neutralizing Antibodies in a Cohort of Homosexual Men: Result of a 6 Year Prospective Study", *AIDS Research in Human Retroviruses* (1988) 4:343–350.

McPhee et al., "Recognition of envelope and tat protein synthetic peptide analogs by HIV positive sera or plasma", *F.E.B.* (1988) 233:393–396.

(List continued on next page.)

*Primary Examiner*—Robert D. Budens
*Attorney, Agent, or Firm*—Richards, Medlock & Andrews

[57] ABSTRACT

Disclosed is a human monoclonal antibody produced by the hybridoma designated Clone 3 and having A.T.C.C. Accession No. CRL 10198. The Clone 3 human monoclonal antibody immunologically binds to a conserved epitope on the transmembrane envelope glycoprotein gp41 of Human Immunodeficiency Virus Type 1 (HIV-1) having the amino acid sequence GCSGKLIC.

2 Claims, 8 Drawing Sheets

OTHER PUBLICATIONS

McPhee et al., "Putative Contact Prototopes for HIV–1 Envelope Proteins gp120/gp41: Antiviral Action of Synthetic Peptide Analogs" from the Cold Spring Harbor Symposium (Sep. 1988), p. 17.

Jackson et al., "Passive Immunoneutralisation of Human Immunodeficiency Virus in Patients with Advanced AIDS", *Lancet* (1988) 2;647–652.

Karpas et al., "Effects of passive immunization of patients with the acquired immunodeficiency syndrome–related complex and acquired immunodeficiency syndrome", *Proceedings of the National Academy of Science* (U.S.A.) (1988) 5:9234–9237.

Book entitled *Anti–Idiotypes, Receptors, and Molecular Mimicry* (1988) by D. Scott Linthicum and Nadir R. Farid.

Johnson et al., "Site–Directed ELISA Identifies a Highly Antigenic Region of the Simian Immunodeficiency Virus Transmembrane Glycoprotein", *AIDS Research and Human Retroviruses* (1988) 4:159–164.

Kowalski et al., "Functional Regions of the Envelope Glycoprotein of Human Immunodeficiency Virus Type 1", *Science* (1987) 237:1351–1355.

Matthews et al., "Prospects for Development of a Vaccine Against HTLV–III–Related Disorders", *AIDS Research and Human Retroviruses* (1987) 3;197–206.

Chiodi et al., "Site–Directed ELISA with Synthetic Peptides Representing the HIV Transmembrane Glycoprotein", *J. of Medical Virology* (1987) 23:1–9.

Gnann, Jr. et al. "Synthetic Peptide Immunoassay Distinguishes HIV Type 1 and HIV Type 2 Infections", *Science* (1987) 237:1346–1349.

Franchini et al., "Sequence of simian immunodeficiency virus and its relationship to the human immunodeficiency viruses", *Nature* (1987) 328:539–543.

Desrosiers et al., "Animal Models for Acquired Immunodeficiency Syndrome", *Reviews of Infectious Diseases* (1987) 9:438–445.

Chakrabarti et al., "Sequence of simian immunodeficiency virus from macaque and its relationship to other human and simian retroviruses", *Nature* (1987) 328:543–547.

R. S. Smith et al., "Antibody to a Synthetic Oligopeptide in Subjects at Risk for Human Immunodeficiency Virus Infection", *J. Clinical Microbiology* (1987) 25:1498–1504.

Gnann, Jr. et al., "Diagnosis of AIDS by Using a 12–Amino Acid Peptide Representing an Immunodominant Epitope of the Human Immunodeficiency Virus", *Journal of Infectious Diseases* (1987) 156:261–267.

Norrby et al., "Discrimination between antibodies to HIV and to related retroviruses using site–directed serology", *Nature* (1987) 329:248–250.

Gnann, Jr. et al., "Fine Mapping of an Immunodominant Domain in the Transmembrane Glycoprotein of Human Immunodeficiency Virus", *Journal of Virology* (1987) 61:2639–2641.

Banapour et al., "Characterization and Epitope of a Human Monoclonal Antibody Reactive with the Envelope Glycoprotein of Human Immunodeficiency Virus", *Journal of Immunology* (1987) 139:4027–4033.

Modrow et al., "Computer–Assisted Analysis of Envelope Protein Sequences of Seven Human Immunodeficiency Virus Isolates: Prediction of Antigenic Epitopes in Conserved and Variable Regions", *Journal of Virology* (1987) 61:57–578.

The chapter "Use of Heteromyelomas in the Enhancement of Human Monoclonal Antibody Production" by Nelson H. Teng and Marcia Bieber from the book *Methods of Hybridoma Formation* (1987), pp. 257–271.

The chapter "Detection of Antibodies to HIV Using Synthetic Peptides Derived from the gp41 Envelope Protein" by Rosen et al., from the book *Vaccines 87* (1987), pp. 188–193.

Lifson et al., "Induction of CD4–dependent cell fusion by the HTLV–III/LAV envelope glycoprotein", *Nature* (1986) 322:725–728.

Rasheed et al., "Virus–Neutralizing Activity, Serologic Heterogeneity, and Retrovirus Isolation from homosexual Men in the Los Angeles Area", *Virology* (1986) 150:1–9.

Wang et al., "Detection of antibodies to human T–lymphotropic virus type III by using a synthetic peptide of 21 amino acid residues corresponding to a highly antigenic segment of gp41 envelope protein", *Proceedings of the National Academy Science* (U.S.A.) (1986) 83:6159–6163.

Putney et al., "HTLV–III/LAV–Neutralizing Antibodies to an *E. coli*–Produced Fragment of the Virus Envelope", *Science* (1986) 234:1392–1395.

Robert–Guroff et al., "HTLV–III–neutralizing antibodies in patients with AIDS and AIDS–related complex", *Nature* (1985) 316:72–74.

Chang et al., "Detection of Antibodies to Human T–Cell Lymphotropic Virus–III (HTLV–III) with an Immunoassay Employing a Recombinant *Escherichia Coli*–Derived Viral Antigenic Peptide", *J. Bio/Technology* (1985) 3:905–909.

Dalgleish et al., "The CD4(T4) antigen is an essential component of the receptor for the AIDS retrovirus", *Nature* (1984) 312:763–766.

Broder et al., "A Pathogenic Retrovirus (HTLV–III) Linked to AIDS", *New England Journal of Medicine* (1984) 311:1292–1297.

Carrasquillo et al., "Diagnosis of and Therapy for Solid Tumors with Radiolabeled Antibodies and Immune Fragments", *Cancer Treatment Reports* (1984) 68:317–328.

James T. Barrett, *Textbook of Immunology—An Introduction to Immunochemistry and Immunobiology*, The C. V. Mosby Company, 1983, pp. 41–42.

*Journal of Virology*, vol. 64, No. 9, Sep., 1990, pp. 4123–4129, Bugge et al.

Gowland, Peter, et al., "Phase I/IIA clinical Studies of A Chimeric Mouse–Human Monoclonal Antibody to HIV–1 gp120", VIIIth International Conference on AIDS, Amsterdam, Jul. 19–24, 1992 PoB 3445, p. B161.

Mathiesen, T.; Chiodo, F.; Broliden, P. A.; Albert, J.; Houghten, R. A.; Utter, G.; Wahren, B.; Norrby, E., (1989) "Analysis of a Subclass–Restricted HIV–1 gp41 Epitope by Omission Peptides", *Immunology*, 67:1–7.

Broliden, Per A.; Moschese, Viviana; Ljunggren, Kristina; Rosen, Jonathan; Fundaro, Carlo; Plebani, Anna; Jondal, Mikael; Rossi, Paolo; Wahren, Britta, (1989) "Diagnostic Implication of Specific Immunoglobulin G Patterns of Children Born to HIV–Infected Mothers", *AIDS*, 3:577–582.

Ruden, U.; Trojnar, J.; Solver, E.; Wahren, B., Abstract of "Accuracy of Single Peptide Anti–HIV Assays", *Eleventh American Peptide Symposium*, Jul. 9–14, 1989.

Neurath, Robert A., et al., (1990), "Epitope Scanning of HIV–1 Envelope Glycoproteins: Confronting the Sequence Hypervariability", *Vaccines 90*, pp. 283–289.

Emini, Emilio A., et al., (Aug. 1990), "Antibody–Mediated In Vitro Neutralization of Human Immunodeficiency Virus Type 1 Abolishes Infectivity for Chimpanzees", *Journal of*

*Virology*, 64:3674–3678.

Geysen, H. Mario, et al., (Jul. 1984), "Use of Peptide Synthesis to Probe Viral Antigens for Epitopes to a Resolution of a Single Amino Acid", *Proc. Natl. Acad. Sci. USA*, 81:3998–4002.

Ugen, Kenneth E., et al., (Jun. 1992), "Vertical Transmission of Human Immunodeficiency Virus (HIV) Infection. Reactivity of Maternal Sera With Glycoprotein 120 and 41 Peptides from HIV Type 1", *J. Clin. Invest.* 89:1923–1930.

Q. J. Sattentau and J. P. Moore, "Conformational Changes Induced in the Human Immunodeficiency Virus Envelope Glycoprotein by Soluble CD4 Binding", *The Academic Department of Genito–Urinary Medicine*, vol. 174, Aug. 1991, pp. 407–415.

John P. Moore, et al., "Antigenic Variation in gp120s from Molecular Clones of HIV–1 LAI", *Aids Research and Human Retroviruses*, vol. 9, No. 12, 1993, pp. 1185–1193.

John P. Moore, et al., "Antibodies to Discontinuous or Conformationally Sensitive Epitopes on the gp120 Glycoprotein of Human Immunodeficiency Virus Type 1 Are Highly Prevalent in Sera of Infected Humans", *Journal of Virology*, Feb. 1993, pp. 863–875.

Markus Thali, et al., "Characterization of Conserved Human Immunodeficiency Virus Type 1 gp120 Neutralization Epitopes Exposed upon gp120–CD4 Binding", *Journal of Virology*, Jul. 1993, pp. 3978–3988.

John P. Moore, et al., "Immunochemical Analysis of the gp120 Surface Glycoprotein of Human Immunodeficiency Virus Type 1: Probing the Structure of the C4 and V4 Domains and the Interaction of the C4 Domain With the V3 Loop", *Journal of Virology*, Aug. 1993, pp.4785–4796.

John P. Moore, et al., "Probing the Structure of the V2 Domain of Human Immunodeficiency Virus Type 1 Surface Glycoprotein gp120 With a Panel of Eight Monoclonal Antibodies: Human Immune Response to the V1 and V2 Domains", *Journal of Virology*, Oct. 1993, pp. 6136–6151.

John P. Moore, et al., "Probing the Structure of the Human Immunodeficiency Virus Surface Glycoprotein gp120 With a Panel of Monoclonal Antibodies", *Journal of Virology*, Jan. 1994, pp. 469–484.

*ABI Advanced Technologies*, Catalogue, 1994.

Zolla–Pazner, Susan, et al., (1992), "Passive Immunization for the Prevention and Treatment of HIV Infection", *AIDS*, 6:1235–1247.

Zolla–Pazner, Susan, et al., (1992), "Characteristics of Human Neutralizing Antibodies Derived from HIV–1 Infected Individuals", *Seminars in Virology*, 3:203–211.

Gorny, Miroslaw K., et al., "Specific Immunity to HIV and Other Retroviral Infections", *Progress in AIDS Pathology*, edited by Rotterdam, H., et al., New York, Field & Wood Publications, 1989:181–199.

Emini, E. A., et al., (1992), "Prevention of HIV–1 Infection in Chimpanzees by gp120 V3 Domain–Specific Monoclonal Antibody", *Nature*, 355:728–730.

Condie, Richard M., et al., (1984), "Prevention of Cytomegalovirus Infection in Bone Marrow Transplant Recipients by Prophylaxis With an Intravenous, Hyperimmune Cytomegalovirus Globulin", *Birth Defects*, 20:327–344.

Perrillo, Robert P., et al., (1987), "Immune Globulin and Hepatitis B Immune Globulin", *Arch. Intern Med.*, 144:81–85.

Snydman, David R., et al., (1987), "Use of Cytomegalovirus Immune Globulin to Prevent Cytomegalovirus Disease in Renal–Transplant Recipients", *N. Engl. J. Med.*, 317:1049–1054.

Seeff, Leonard B., et al., (1986), "Passive and Active Immunoprophylaxis of Hepatitis B", *Gastroenterology*, 86:958–981.

Sears, Henry F., (1984), "Effects of Monoclonal Antibody Immunotherapy on Patients with Gastrointestinal Adenocarcinoma", *J. Biol. Response Mod.*, 3;138–150.

Ziegler, Elizabeth J., et al., (1991), "Treatment of Gram–Negative Bacteremia and Septic Shock With HA–1A Human Monoclonal Antibody Against Endotoxin", *N. Engl. J. Med.*, 324:429.

Emini, Emilio A., "Passive Immunization With a Monoclonal Antibody Directed to the HIV–1 gp120 Principal Neutralization Determinant Confers Protection Against HIV–1 Challenge in Chimpanzees", as reported at the VIIth International Conference on AIDS in Florence, Italy, Jun. 16–21, 1991, Abstract No. ThA64, p. 72.

Karpas, Abraham, et al., (1990), "Polymerase Chain Reaction Evidence for Human Immunodeficiency Virus 1 Neutralization by Passive Immunization in Patients With AIDS and AIDS–Related Complex", *Proceedings of the National Academy of Science (U.S.A.)*, 87:7613–7617.

Karpas, Abraham, et al., (1990), "Passive Immunization in ARC and AIDS", *Biotherapy*, 2:159–172.

Geysen, H. Mario, et al., (1987), "Strategies for Epitope Analysis Using Peptide Synthesis", *J. Immunol. Methods*, 102:259–274.

Prince, Alfred M., (1991), "Prevention of HIV Infection by Passive Immunization with HIV Immunoglobulin", *AIDS Research and Human Retroviruses*, 7:971–973.

```
SIV     (606-628)    AIEKYLEDQAQLNAWGCAFRQVC
HIV-2   (581-603)    AIEKYLQDQARLNSWGCAFRQVC
HIV-1   (582-604)    AVERYLKDQQLLGIWGCSGKLIC
```

FIG 3 gp160 H₂N ———————————— COOH   856 amino acids gp120 H₂N ———————————— COOH (amino acid #518-Arg)   518 amino acids gp41   (amino acid #519-Ala) H₂N ———————————— COOH   338 amino acids p121  82 amino acids   (amino acid #565-Glu) H₂N ———————————— COOH (amino acid #646-Leu)

FUSION-ASSOCIATED EPITOPE 12 amino acids (amino acid #598-Leu) H₂H ———————————— COOH (amino acid #609-Cys)

FUSION-ASSOCIATED EPITOPE 12 amino acid sequence: Leu-Gly-Ile-Trp-Gly-Cys-Ser-Gly-Lys-Leu-Ile-Cys

*FIG. 4*

Peptide 2    (amino acids #598-609)
Leu-Gly-Ile-Trp-<u>Gly-Cys-Ser-Gly-Lys-Leu-Ile-Cys</u>

Peptide 6120    (amino acids #602-618)
<u>Gly-Cys-Ser-Gly-Lys-Leu-Ile-Cys</u>-Thr-Thr-Ala-Val-Pro-Trp-Asn-Ala-Ser Octapeptide    (Amino Acid Sequence Common to Both Peptide 2 and Peptide 6120) (amino acids #602-609)
<u>Gly-Cys-Ser-Gly-Lys-Leu-Ile-Cys</u> (Fusion-Associated Epitope)    (R = 1 = Gly)

*FIG. 5*

Linear Representation of Amino Acid Sequences (three letter abbreviation)

Contained within the Transmembrane Glycoprotein gp41 of HIV-1 for Peptide 237 and Peptide 238

Peptide 237   (amino acids #597-611)

Leu-Leu-Gly-Ile-Trp-Gly-Cys-Ser-Gly-Lys-Leu-Ile-Cys-Thr-Thr

Peptide 238 (amino acids #602-616)

Gly-Cys-Ser-Gly-Lys-Leu-Ile-Cys-Thr-Thr-Ala-Val-Pro-Trp-Asn

Decapeptide (Amino Acid Sequence Common to Both Peptide 237 and Peptide 238) (amino acids #602-611)

Gly-Cys-Ser-Gly-Lys-Leu-Ile-Cys-Thr-Thr (The Fusion-Associated Epitope, Gly-Cys-Ser-Gly-Lys-Leu-Ile-Cys, is an octapeptide contained within the decapeptide)

*FIG. 7*

Immunofluorescence Profiles by Flow Cytometry

Fluorescence profiles of [A] HIV-infected Sup-T1 cells and [B] uninfected Sup-T1 cells, stained with human immunodeficiency virus-specific human monoclonal antibody (Clone 3 Antibody), directed against the transmembrane (TM) envelope gp41 fusion-associated octapeptide epitope with the amino acid sequence GCSGKLIC.

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( i x ) FEATURE:
( A ) NAME/KEY: Domain
( B ) LOCATION: 1..8
( D ) OTHER INFORMATION: /label=Epitope
/ note="A neutralizable epitope of gp41 of HIV-1, as identified using monoclonal ATCC CRL 10198, is contained within this sequence or a portion thereof.

( x i ) SEQUENCE DESCRIPTION: SEQ ID NO:1:

Gly Cys Ser Gly Lys Leu Ile Cys
1 5

( 2 ) INFORMATION FOR SEQ ID NO:2:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:2:

Leu Gly Ile Trp Gly Cys Ser Gly Lys Leu Ile Cys
1 5 10

( 2 ) INFORMATION FOR SEQ ID NO:3:

( i ) SEQUENCE CHARACTERISTICS:
( A ) LENGTH: 12 amino acids
( B ) TYPE: amino acid
( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:3:

Leu Asn Ala Trp Gly Cys Ala Phe Arg Gln Val Cys
1               5                   10

( 2 ) INFORMATION FOR SEQ ID NO:4:

( i ) SEQUENCE CHARACTERISTICS:
    ( A ) LENGTH: 12 amino acids
    ( B ) TYPE: amino acid
    ( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:4:

Leu Asn Ser Trp Gly Cys Ala Phe Arg Gln Val Cys
1               5                   10

( 2 ) INFORMATION FOR SEQ ID NO:5:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:5:

Gly Cys Ser Gly Lys Leu Ile Cys Thr Thr Ala Val Pro Trp Asn Ala
1               5                   10                  15
Ser ( 2 ) INFORMATION FOR SEQ ID NO:6:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:6:

Ala Val Glu Arg Tyr Leu Lys Asp Gln Gln Leu Leu Gly Ile Trp
1               5                   10                  15

( 2 ) INFORMATION FOR SEQ ID NO:7:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:7:

```
Leu Lys Asp Gln Gln Leu Leu Gly Ile Trp Gly Cys Ser Gly Lys
1               5                   10                  15
```

( 2 ) INFORMATION FOR SEQ ID NO:8:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:8:

```
Leu Leu Gly Ile Trp Gly Cys Ser Gly Lys Leu Ile Cys Thr Thr
1               5                   10                  15
```

( 2 ) INFORMATION FOR SEQ ID NO:9:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:9:

```
Gly Cys Ser Gly Lys Leu Ile Cys Thr Thr Ala Val Pro Trp Asn
1               5                   10                  15
```

( 2 ) INFORMATION FOR SEQ ID NO:10:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:10:

```
Leu Ile Cys Thr Thr Ala Val Pro Trp Asn Ala Ser Trp Ser Asn
1               5                   10                  15
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:11:

```
Ala Val Pro Trp Asn Ala Ser Trp Ser Asn Lys Ser Leu Glu Gln
1               5                   10                  15
```

( 2 ) INFORMATION FOR SEQ ID NO:12:

( i ) SEQUENCE CHARACTERISTICS:
      ( A ) LENGTH: 9 amino acids
      ( B ) TYPE: amino acid
      ( D ) TOPOLOGY: circular ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:12:

```
Cys Ser Gly Lys Leu Ile Cys Thr Thr
1               5
```

( 2 ) INFORMATION FOR SEQ ID NO:13:

( i ) SEQUENCE CHARACTERISTICS:
      ( A ) LENGTH: 25 amino acids
      ( B ) TYPE: amino acid
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:13:

```
Ile Lys Gln Leu Gln Ala Arg Ile Leu Ala Val Glu Arg Tyr Leu Lys
1               5                   10                  15

Asp Gln Gln Leu Leu Gly Ile Trp Gly
                20                  25
```

( 2 ) INFORMATION FOR SEQ ID NO:14:

( i ) SEQUENCE CHARACTERISTICS:
      ( A ) LENGTH: 20 amino acids
      ( B ) TYPE: amino acid
      ( D ) TOPOLOGY: circular ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:14:

```
Gly Ile Trp Gly Cys Ser Gly Lys Leu Ile Cys Thr Thr Ala Val Pro
1               5                   10                  15

Trp Asn Ala Ser
                20
```

( 2 ) INFORMATION FOR SEQ ID NO:15:

( i ) SEQUENCE CHARACTERISTICS:
      ( A ) LENGTH: 28 amino acids
      ( B ) TYPE: amino acid
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:15:

Asp Ile Ile Ser Leu Trp Asp Gln Ser Leu Lys Pro Cys Val Lys Leu
1               5                   10                  15

Thr Pro Leu Cys Val Ser Leu Lys Cys Thr Asp Leu
            20              25

( 2 ) INFORMATION FOR SEQ ID NO:16:

( i ) SEQUENCE CHARACTERISTICS:
       ( A ) LENGTH: 30 amino acids
       ( B ) TYPE: amino acid
       ( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:16:

His Glu Asp Ile Ile Ser Leu Trp Asp Gln Ser Leu Lys Pro Cys Val
1               5                   10                  15

Lys Leu Thr Pro Leu Cys Val Ser Leu Lys Cys Thr Asp Leu
                20              25                  30

( 2 ) INFORMATION FOR SEQ ID NO:17:

( i ) SEQUENCE CHARACTERISTICS:
       ( A ) LENGTH: 30 amino acids
       ( B ) TYPE: amino acid
       ( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:17:

Gln Ala Arg Ile Leu Ala Val Glu Arg Tyr Leu Lys Asp Gln Gln Leu
1               5                   10                  15

Leu Gly Ile Trp Gly Cys Ser Gly Lys Leu Ile Cys Thr Thr
                20              25                  30

( 2 ) INFORMATION FOR SEQ ID NO:18:

( i ) SEQUENCE CHARACTERISTICS:
       ( A ) LENGTH: 9 amino acids
       ( B ) TYPE: amino acid
       ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:18:

Gly Cys Ser Gly Lys Leu Ile Cys Thr
1               5

( 2 ) INFORMATION FOR SEQ ID NO:19:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:19:

Cys Ser Gly Lys Leu Ile Cys Thr
1                5

( 2 ) INFORMATION FOR SEQ ID NO:20:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:20:

Cys Ser Gly Lys Leu Ile Cys
1                5

( 2 ) INFORMATION FOR SEQ ID NO:21:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:21:

Gly Cys Ser Gly Lys Leu Ile Cys Thr Thr
1                5                   10

( 2 ) INFORMATION FOR SEQ ID NO:22:

( i ) SEQUENCE CHARACTERISTICS:
      ( A ) LENGTH: 23 amino acids
      ( B ) TYPE: amino acid
      ( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:22:

Ala Ile Glu Lys Tyr Leu Glu Asp Gln Ala Gln Leu Asn Ala Trp Gly
1                5                   10                  15

Cys Ala Phe Arg Gln Val Cys
                20

( 2 ) INFORMATION FOR SEQ ID NO:23:

( i ) SEQUENCE CHARACTERISTICS:
      ( A ) LENGTH: 23 amino acids
      ( B ) TYPE: amino acid
      ( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:23:

```
Ala  Ile  Glu  Lys  Tyr  Leu  Gln  Asp  Gln  Ala  Arg  Leu  Asn  Ser  Trp  Gly
1                 5                      10                         15
Cys  Ala  Phe  Arg  Gln  Val  Cys
                20
```

( 2 ) INFORMATION FOR SEQ ID NO:24:

( i ) SEQUENCE CHARACTERISTICS:
( A ) LENGTH: 23 amino acids
( B ) TYPE: amino acid
( D ) TOPOLOGY: unknown ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:24:

```
Ala  Val  Glu  Arg  Tyr  Leu  Lys  Asp  Gln  Gln  Leu  Leu  Gly  Ile  Trp  Gly
1                 5                      10                         15
Cys  Ser  Gly  Lys  Leu  Ile  Cys
                20
```

( 2 ) INFORMATION FOR SEQ ID NO:25:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:25:

```
Gln  Leu  Thr  Val  Trp  Gly  Ile  Lys  Gln  Leu  Gln  Ala  Arg  Ile  Leu
1                 5                      10                         15
```

( 2 ) INFORMATION FOR SEQ ID NO:26:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:26:

```
Gly  Ile  Lys  Gln  Leu  Gln  Ala  Arg  Ile  Leu  Ala  Val  Glu  Arg  Tyr
1                 5                      10                         15
```

( 2 ) INFORMATION FOR SEQ ID NO:27:

( i ) SEQUENCE CHARACTERISTICS:
( A ) LENGTH: 15 amino acids
( B ) TYPE: amino acid
( D ) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:27:

```
Gln Ala Arg Ile Leu Ala Val Glu Arg Tyr Leu Lys Asp Gln Gln
1               5                   10                  15
```

(2) INFORMATION FOR SEQ ID NO:28:

(i) SEQUENCE CHARACTERISTICS:
  (A) LENGTH: 12 amino acids
  (B) TYPE: amino acid
  (D) TOPOLOGY: unknown (ii) MOLECULE TYPE: peptide (iii) HYPOTHETICAL: NO (v) FRAGMENT TYPE: internal (xi) SEQUENCE DESCRIPTION: SEQ ID NO:28:

```
Leu Gly Leu Trp Gly Cys Ser Gly Lys Leu Ile Cys
1               5                   10
```

(2) INFORMATION FOR SEQ ID NO:29:

(i) SEQUENCE CHARACTERISTICS:
  (A) LENGTH: 12 amino acids
  (B) TYPE: amino acid
  (D) TOPOLOGY: circular (ii) MOLECULE TYPE: peptide (iii) HYPOTHETICAL: NO (v) FRAGMENT TYPE: internal (xi) SEQUENCE DESCRIPTION: SEQ ID NO:29:

```
Leu Gly Ile Trp Gly Cys Ser Gly Lys Leu Ile Cys
1               5                   10
```

(2) INFORMATION FOR SEQ ID NO:30:

(i) SEQUENCE CHARACTERISTICS:
  (A) LENGTH: 8 amino acids
  (B) TYPE: amino acid
  (D) TOPOLOGY: circular (ii) MOLECULE TYPE: peptide (iii) HYPOTHETICAL: NO (v) FRAGMENT TYPE: internal (xi) SEQUENCE DESCRIPTION: SEQ ID NO:30:

```
Gly Cys Ser Gly Lys Leu Ile Cys
1               5
```

(2) INFORMATION FOR SEQ ID NO:31:

(i) SEQUENCE CHARACTERISTICS:
  (A) LENGTH: 9 amino acids
  (B) TYPE: amino acid
  (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:31:

Cys Ser Gly Lys Leu Ile Cys Thr Thr
1               5

(2) INFORMATION FOR SEQ ID NO:32:

(i) SEQUENCE CHARACTERISTICS:
    (A) LENGTH: 8 amino acids
    (B) TYPE: amino acid
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:32:

Ser Gly Lys Leu Ile Cys Thr Thr
1               5

(2) INFORMATION FOR SEQ ID NO:33:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:33:

Gly Lys Leu Ile Cys Thr Thr
1               5

(2) INFORMATION FOR SEQ ID NO:34:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:34:

Lys Leu Ile Cys Thr Thr
1               5

(2) INFORMATION FOR SEQ ID NO:35:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:35:

```
        Leu  Ile  Cys  Thr  Thr
        1                 5
```

( 2 ) INFORMATION FOR SEQ ID NO:36:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:36:

```
        Ser  Gly  Lys  Leu  Ile  Cys  Thr
        1                  5
```

( 2 ) INFORMATION FOR SEQ ID NO:37:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:37:

```
        Gly  Lys  Leu  Ile  Cys  Thr
        1                  5
```

( 2 ) INFORMATION FOR SEQ ID NO:38:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:38:

```
        Lys  Leu  Ile  Cys  Thr
        1                 5
```

( 2 ) INFORMATION FOR SEQ ID NO:39:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:39:

```
        Leu  Ile  Cys  Thr
        1
```

(2) INFORMATION FOR SEQ ID NO:40:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:40:

```
Ser Gly Lys Leu Ile Cys
1               5
```

(2) INFORMATION FOR SEQ ID NO:41:

(i) SEQUENCE CHARACTERISTICS:
  (A) LENGTH: 5 amino acids
  (B) TYPE: amino acid
  (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:41:

```
Gly Lys Leu Ile Cys
1               5
```

(2) INFORMATION FOR SEQ ID NO:42:

(i) SEQUENCE CHARACTERISTICS:
  (A) LENGTH: 4 amino acids
  (B) TYPE: amino acid
  (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:42:

```
Lys Leu Ile Cys
1
```

HUMAN MONOCLONAL ANTIBODIES DIRECTED AGAINST THE TRANSMEMBRANE GLYCOPROTEIN (GP41) OF HUMAN IMMUNODEFICIENCY VIRUS-1 (HIV-1)

This application is a continuation-in-part of U.S. application Ser. No. 07/396,751, filed Aug. 24, 1989, now pending.

FIELD OF THE INVENTION

This invention relates to anti-HIV-1 monoclonal antibodies and specifically to monoclonal antibodies which bind to a viral epitope, thereby neutralizing the virus. The invention also relates to continuous cell lines capable of producing the antibodies and to the peptides recognizable by the antibodies. The antibodies and antigens of this invention are useful for diagnosis, prognosis, prophylaxis and therapy. This invention also relates to prognostic tests for viral diseases, and particularly prognostic tests for Acquired Immunodeficiency Syndrome (AIDS).

BACKGROUND OF THE INVENTION

The human immunodeficiency virus (HIV-1) has been established as the primary etiologic agent in the pathogenesis of acquired immunodeficiency syndrome (AIDS) and related disorders. (Barre-Sinoussi, et al. *Science* (1983) 220:868–871; Gallo, et al., *Science* (1984) 224:500–503; Levy, et al., *Science* (1984) 225:840–842).

The CD4+ cells play a central role in HIV infection. (Fauci, *Science* (1988) 239:617–622). CD4 is a molecule present on the surface of certain lymphocytes and, to a lesser degree, macrophages. The CD4 molecule plays a significant role in the function of T4 helper lymphocytes and serves as a marker for such cells. (Gallo, R. C. and Montagnier, L., *Scientific American* (1988) 259:41–48.) The virus uses the CD4 receptor to gain entry into a number of cells. (Dalgleish, et al., *Nature* (1984) 312:763–767). The envelope glycoprotein, gp160, is the precursor to the gp120, which specifically binds to the surface receptor (CD4) of CD4+ cells, and the gp41, the transmembrane (TM) glycoprotein which initiates cell-membrane fusion, leading to the formation of multinucleated giant cells commonly called syncytia. (Kowalski, *Science* (1987) 237:1351–1355). Fusion leads to the death of the syncytial cells. While HIV-1 may also cause cell death through mechanisms independent of cell fusion, data suggest that the formation of syncytia contributes to the progressive depletion of CD4+ cells (T4 helper lymphocytes), quantitatively and functionally. (Lifson, et al., *Nature* (1986) 323:725–728). This is the most profound hematologic feature and hallmark associated with acquired immunodeficiency syndrome (AIDS) (Broder, S. M. and Gallo, R. C., *N. Eng. J. Med.* (1984) 311:1292–1297), as demonstrated by impaired cell-mediated immunity.

Infection of humans with HIV-1 leads to a humoral immune response by B lymphocytes resulting in the production of antibodies directed against most of the viral structural antigens. A particular subset of antibodies is directed against HIV envelope antigens (gp120 and gp41) which may be involved in induction of active immunity. (Matthews, et al., *AIDS Research and Human Retroviruses* (1987) 3:197–206). Neutralization assays with sera from HIV-infected individuals (Robert-Guroff, et al., *Nature* (1985) 316:72–74; Rasheed, et al., *Virology* (1986) 150:1–9) or from immunized animals, suggest that the envelope glycoprotein contains epitope(s) that elicit antibodies capable of neutralizing HIV infection in vitro. As an in vivo corollary, it has been demonstrated that high neutralizing antibody titers correlated with a better clinical outcome, and low or decreasing neutralizing antibody titer signaled poor prognosis. (Robert-Guroff, et al., *AIDS Research and Human Retroviruses* (1988) 4:343–350). A decrease in average antibody titers has been clinically observed in late stages of infection, particularly with regard to antibodies directed against the HIV envelope epitopes and specifically against the TM gp41 region containing the amino acid sequence against which the herein described human monoclonal antibody is biologically reactive. (Shafferman, et al., *AIDS Research and Human Retroviruses* (1989) 5:33–39; Chiodi, et al., *J. Med. Virol.* (1987) 23:1–9; McPhee, et al., *FEBS Lett.* (1988) 233:393–396).

Measures capable of boosting the neutralizing antibody titer of individuals already infected with the virus, eliciting high-titer neutralizing antibodies (i.e., active immunotherapy), or increasing neutralizing antibodies (i.e., passive immunotherapy) in individuals at risk would prove beneficial in controlling viral spread in vivo or in preventing new infection. (Robert-Guroff, et al., *AIDS Research and Human Retroviruses* (1988) 3:343–350).

The present invention makes possible the measures cited above. Any attempts at passive immunotherapy will require the production of large quantities of antibody on a routine basis. The development of a continuous cell line accommodates this. The monoclonality of the antibody enables the administration of reactive physiological amounts of the antibody since all of the antibody being administered is directed against the biologically active epitope of the virus, unlike polyclonal serums which contain antibodies against other structural proteins as well. The potential immunogenicity of the peptide sequence of this epitope, as evidenced by the immunogenicity of a peptide of similar sequence, will enable safe and effective vaccination of individuals, thereby avoiding the great risks involved in immunizing with attenuated or even killed viruses.

The present invention is further directed to a kit and a method for detecting the presence and determining concentration of an antibody that inhibits HIV-1 fusion-associated epitope, a peptide on gp41 with the amino acid sequence represented by GCSGKLIC (SEQ NO:1). The detection and quantitation method includes an enzyme-linked immunosorbent assay (ELISA).

The determination of the concentration of the antibody that inhibits HIV-1 fusion-associated epitope on gp41, present in body fluids of a patient seropositive for HIV-1 antibodies, provides the physician with an objective means to form a prognosis for each individual case and assists the clinician therefore in determining the appropriateness to initiate medical intervention or change therapy.

SUMMARY OF THE INVENTION

The present invention is concerned with a novel human monoclonal antibody which defines and neutralizes a biologically functional antigenic/immunogenic site on the HIV-1 transmembrane (TM) envelope glycoprotein.

The invention of the human monoclonal antibody, the production of the antibody, the identification of the epitope (peptide) to which the antibody binds, and the delineation of the biologically important function of the defined epitope, are achieved and described in detail by the following outlined immunochemical methods and biological assays.

The antigenic/immunogenic peptide identified as the epitope (target antigen) is contained within the twelve amino acid (L-form) sequence: leucine-glycine-isoleucine-tryptophan-glycine-cysteine-serine-glycine-lysine-leucine -isoleucine-cysteine (SEQ. No. 2). Since antigenic determinants have been reported to be represented by as few as five amino acid residues, the actual epitope may be a truncation of this sequence. (Barrett, J. T., *Textbook of Immunology* (1983) p. 41). Specifically, the human monoclonal antibody immunochemically binds to a conserved peptide of the HIV-1 transmembrane (TM) glycoprotein designated gp41, and, as a consequence of this antibody-antigen reaction, biologically blocks syncytia formation between HIV-1 virally infected human lymphocytes and uninfected lymphocytes (CD4+ cells).

The described human monoclonal antibody binds to the identified viral epitope, specifically leucine-glycine-isoleucine-tryptophan-glycine-cysteine-serine-glycine -lysine-leucine-isoleucine-cysteine, and the fusion of HIV-1-infected CD4+ cells with non-infected CD4+ cells is thereby blocked. Cell fusion is a biologically functional process that can therefore be ascribed to this conserved immunodominant region.

The human monoclonal antibody described (Anti-gp41) inhibits fusion of CD4+ cells caused by HIV-1 and therefore blocks infection via binding to the gp41 transmembrane glycoprotein, specifically the fusion-associated epitope as delineated. This inhibition signifies the utility of Anti-gp41 in passive immunotherapy. Other fusion-inhibiting agents, such as synthetic inhibitory peptides, are also disclosed. Administration of the retrovirus/vaccine containing the immunogenic fusion-associated epitope/subunit will elicit fusion blocking antibody (as evidenced by the human B cell line identified from the HIV-1-infected, naturally immunized, patient/donor), thereby providing protection against the infection and depletion of CD4+ cells and, therefore, preventing the development of acquired immunodeficiency syndrome. This protection evidences the utility of gp41, or an appropriate subunit thereof, in active immunotherapy.

BRIEF DESCRIPTION OF THE DRAWINGS

For a more complete understanding of the present invention and for further advantages thereof, reference is made to the following Detailed Description taken in conjunction with the accompanying Drawings, in which:

FIG. 1 is a depiction of the Western blot described in Example 3;

FIG. 2 is a graph of the results of the syncytium-forming microassay described in Example 11;

FIG. 3 presents the 23 amino acid peptide sequences for SIV, used in the ELISA by Johnson et al., as reported in *AIDS Research and Human Retroviruses* (1988) 4:159–164, and the analogous regions for HIV-2 and HIV-1;

FIG. 4 illustrates a linear comparison of the peptide sequences tested in determining the specificity of Anti-gp41;

FIG. 5 presents the linear representation of amino acid sequences (three letter abbreviation) contained within the transmembrane glycoprotein gp41 of HIV-1 for Peptide 2 and Peptide 6120;

FIG. 6 illustrates the fine epitope mapping for Peptides 232–240;

FIG. 7 presents the linear representation of amino acid sequences (three letter abbreviation) contained within the transmembrane glycoprotein gp41 of HIV-1 for Peptide 237 and Peptide 238;

FIG. 8 shows the reduced and non-reduced Western Blot for the donor patient plasma and for Clone 3 antibody; and FIG. 9 illustrates immunofluorescence profiles by flow cytometry for HIV-infected Sup-T1 cells and uninfected Sup-T1 cells.

DETAILED DESCRIPTION OF THE INVENTION

The subject invention is to novel human monoclonal antibodies that are biologically reactive against a specific immunodominant peptide region within the transmembrane glycoprotein gp41 envelope component of the human immunodeficiency virus (HIV-1), delineation of the peptide region (epitope) to which the human monoclonal antibody binds, and immunologic description of the associated biological function of the epitope. The invention also encompasses the specific immunologically reactive and biologically functional analogous peptide regions (immunogens) on HIV-2 and SIV to elicit the production of corresponding neutralizing antibodies against HIV-2 in humans, and SIV in non-human primates.

The following describes the creation of cells which are capable of producing, in Vitro, ad infinitum, human monoclonal antibodies that are biologically active against the transmembrane glycoprotein gp41 of HIV-1.

Based on the fact that mononuclear cells circulating in the peripheral blood of HIV-1-infected individuals produce antibodies against HIV antigens, an asymptomatic patient who had high titers of plasma antibodies against HIV was selected as a donor of B-lymphocytes. The B-lymphocytes collected from this patient were subsequently transformed by Epstein-Barr Virus (EBV). Seven anti-HIV antibody-producing human lymphoblastoid cell lines have been obtained in this manner and have been stable with respect to antibody production. In order to further assure stability and augment antibody production, an aliquot of each of the created EBV transformed human cell lines has been fused with a heteromyeloma (mouse-human hybrid myeloma) as a fusion partner to produce a hybridoma counterpart.

Supernatants from the resultant hybridomas were screened for antibodies against HIV. Cell lines testing positive for anti-HIV antibody production were subcloned twice and secreted antibody was then tested specifically for binding against the envelope glycoproteins of the virus (i.e., gp41 and gp120). One of seven human monoclonal antibodies testing positive for anti-gp41 reactivity (designated Clone 3 antibody) has been purified from the cell culture supernatants by affinity chromatographic techniques. This human monoclonal antibody (not an animal derived monoclonal antibody) has been demonstrated to have biological activity at physiologic concentrations against HIV-1 (specifically HTLV-IIIB) in a fusion (syncytium) inhibition, in vitro assay; and in neutralization of free HIV-1 (specifically SF2) infectivity of human mononuclear cells in culture. The specific level of fusion inhibition and inhibition of free virus infectivity achieved is detailed in Example 11 and Example 18, respectively, discussed hereinafter.

Development of Clone 3 cell line is detailed further in Example 1 discussed hereinafter. Clone 3 was deposited with the American Type Culture Collection (ATCC) in Rockville, Md. on Aug. 10, 1989 and received accession number ATCC CRL 10198.

Additionally, the specific amino acid sequence (epitope) to which the human monoclonal antibody binds has been ascertained, thereby ascribing the associated biological function of cell fusion to the epitope (fusion-associated epitope). Epitope mapping is discussed hereinafter in Example 8, Example 9, and Example 10.

Other investigators have utilized knowledge of antigenic epitopes to develop "complementary" peptides that are capable of inhibiting epitope-epitope (prototopes) binding or inhibiting the binding of an enzyme to its substrate. (McPhee, et al., Cold Spring Harbor Symposium (1988) p. 17; Lambert, et al., V International Conference on AIDS (1989), Abstract No. W.C.O.11, p. 526). In either instance, development of complementary peptides is facilitated since a complementary peptide already exists and has been tested in nature. Such peptides were found to inhibit production of the mature viral proteins reverse transcriptase and p24, or to inhibit or delay syncytia formation.

Similarly, a complementary peptide could be synthesized which would be capable of binding to the gp41 fusion-associated epitope disclosed, thereby preventing fusion between HIV-1-infected and uninfected cells. The synthetic peptide could then be administered therapeutically.

The biological reactivity of the monoclonal antibody and the biological function of the epitope to which it binds reveal the invention's utility for passive and active therapeutic intervention in the treatment of acquired immunodeficiency syndrome. Specifically, data to support the efficacy of passive immunotherapy in chimpanzees have been published, for it has been determined that neutralization of in vivo HIV-1 infectivity can be mediated by in vitro neutralizing antibody directed against the gp120 major, yet hypervariable, neutralizing epitope. (Emini, et al., V. International Conference on AIDS (1989), Abstract No. Th.C.O.30, p. 538). The human monoclonal antibody can be administered to patients who lack neutralizing antibodies against this epitope within gp41, thereby providing passive immunotherapy. In a parallel human study, data from recent clinical trials (Jackson, et al., *Lancet* (1988) 2:647–652; Karpas, A., *Proc. Natl. Acad. of sciences* (U.S.A.) (1988) 85:9234–9237) have demonstrated that passive immunization improved the status of patients with advanced AIDS. In those trials, passive immunization was accomplished by transfusing plasmas containing antibodies from asymptomatic AIDS patients into the symptomatic AIDS recipients.

In a similar approach, another therapeutic use of the monoclonal antibody of the present invention is the active immunization of a patient using an anti-idiotypic antibody raised against one of the present monoclonal antibodies. Immunization with an anti-idiotype which mimics the structure of the fusion-associated epitope could elicit an active anti-gp41 response. (Linthicum, D. S. and Farid, N. R., *Anti-Idiotypes, Receptors, and Molecular Mimicry* (1988), pp. 1–5 and 285–300).

Likewise, active immunization can be induced by administering the antigenic and immunogenic immunodominant epitope as a component of a subunit vaccine. Vaccination could be performed orally or parenterally in amounts sufficient to enable the recipient to generate protective fusion inhibiting (neutralizing) antibodies against this biologically functional region, prophylactically or therapeutically. Additionally, the peptide leucine-glycine-leucine-tryptophan-glycine-cysteine-serine -glycine-lysine-leucine-isoleucine-cysteine (SEQ NO:28), or a truncated version thereof, may be used in place of the native peptide sequence disclosed as the fusion-associated epitope, since this peptide has been shown to be capable of equivalently binding polyclonal antibodies which recognize the native epitope containing an isoleucine instead of a leucine at the third amino acid position in the sequence above. (Gnann, et al., *Science* (1987) 237:1346–1349).

The twelve amino acid residue peptide which is immunologically reactive with the HIV-1 specific fusion blocking human monoclonal antibody, described immunochemically and biologically in the text, is useful in compositions of subunit vaccines to elicit the production of protective fusion blocking antibodies against HIV-1 in animals including man. The host can be actively immunized with the antigenic/immunogenic peptide in pure form, a fragment of the peptide, or a modified form of the peptide.

One or more amino acids, not corresponding to the original protein sequence, can be added to the amino or carboxyl terminus of the original 12-mer (i.e., 12 amino acid peptide), or truncated 11-mer, 10-mer, 9-mer, 8-mer, or even 7-mer peptides. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof.

Alternative protein modification techniques may be used, e.g., $NH_2$-acetylation or COOH-terminal amidation, to provide additional means for coupling the peptide to another protein or peptide molecule or to a support.

The novel peptide sequence is set forth below in a general formula common to HIV-1, HIV-2, and SIV:

$$X\text{-}a\text{-}b\text{-}c\text{-tryptophan-glycine-cysteine-}x\text{-}x\text{-}x\text{-}x\text{-}x\text{-cysteine-}Y\text{-}Z.$$

The specific novel peptide sequence, and truncated sequences, for each of the comparable analogous conserved immunodominant regions from HIV-1, HIV-2, and SIV are set forth in the following formulae.

For the Human Immunodeficiency Virus-1 (HIV-1), a conserved immunodominant, antigenic/immunogenic twelve amino acid residue peptide (amino acids numbers 598–609, Gnann numbering system, id.), a structural component of the transmembrane glycoprotein gp41, is immunologically reactive with the HIV-1 specific fusion blocking human monoclonal antibody. The novel peptide sequence and the truncated sequences are set forth in the formula below:

$$X\text{-}a_1\text{-}b_1\text{-}c_1\text{-tryptophan-glycine-cysteine-}{}^1x_1\text{-}{}^2x_1\text{-}{}^3x_1\text{-}{}^4x_1\text{-}{}^5x_1\text{-cysteine-}Y\text{-}Z$$

where X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or cysteine; and Z is OH or $NH_2$, and $a_1$ is leucine $b_1$ is glycine $c_1$ is isoleucine ${}^1x_1$ is serine ${}^2x_1$ is glycine ${}^3x_1$ is glycine ${}^4x_1$ is leucine ${}^5x_1$ is isoleucine Alternatively, a truncated peptide can be produced where a is present, with b and c also being present, to represent the original 12-mer; a is absent, with b and c being present, to represent an 11-mer; a and b are absent, with c only being present, to represent a 10-mer; a and b and c are absent, to represent a 9-mer, depicted by the following sequence formula: tryptophan-glycine-cysteine-x-x-x-x-x-cysteine which is common to analogous positions within the three comparable epitopes for HIV-1, HIV-2 and SIV. Similarly, the tryptophan and glycine residues may also be deleted resulting in the production of an 8-mer and 7-mer, respectively.

For the Human Immunodeficiency Virus-2 (HIV-2), a conserved immunodominant, antigenic/immunogenic twelve amino acid residue peptide (amino acids numbers 592–603, Franchini numbering system as reported by Johnson, et al., *AIDS Research and Human Retroviruses* (1988) 4:159–164) which is a structural component of the transmembrane glycoprotein, and the truncated sequences are set forth in the formula below:

$$X\text{-}a_2\text{-}b_2\text{-}c_2\text{-tryptophan-glycine-cysteine-}{}^1x_2\text{-}{}^2x_2\text{-}{}^3x_2\text{-}{}^4x_2\text{-}{}^5x_2\text{-cysteine-Y-Z}$$

where X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or cysteine; and Z is OH or $NH_2$, and $a_2$ is leucine
$b_2$ is asparagine
$c_2$ is serine
${}^1x_2$ is alanine
${}^2x_2$ is phenylalanine
${}^3x_2$ is arginine
${}^4x_2$ is glutamine
${}^5x_2$ is valine Alternatively, a truncated peptide can be produced where a is present, with b and c also being present, to represent the original 12-mer; a is absent, with b and c being present, to represent an 11-mer; a and b are absent, with c only being present, to represent a 10-mer; a and b and c are absent, to represent a 9-mer as described above. The tryptophan and glycine residues may also be deleted resulting in the production of an 8-mer and 7-mer, respectively.

For the simian immunodeficiency virus (SIV), a conserved immunodominant, antigenic/immunogenic twelve amino acid residue peptide (amino acids numbers 617–628, Franchini numbering system, id.), which is a structural component of the transmembrane glycoprotein gp32, and the truncated sequences are set forth in the formula below:

$$X\text{-}a_s\text{-}b_s\text{-}c_s\text{-tryptophan-glycine-cysteine-}{}^1x_s\text{-}{}^2x_s\text{-}{}^3x_s\text{-}{}^4x_s\text{-}{}^5x_s\text{-cysteine-Y-Z}$$

where X is either a H of the amino terminal $NH_2$ group of the peptide or an additional amino acid bonded to the amino terminal $NH_2$ group of the peptide, the additional amino acid being selected to facilitate coupling of the peptide to a carrier protein; Y is absent or cysteine; and Z is OH or $NH_2$, and $a_s$ is leucine
$b_s$ is asparagine
$c_s$ is alanine
${}^1x_s$ is alanine
${}^2x_s$ is phenylalanine
${}^3x_s$ is arginine
${}^4x_s$ is glutamine
${}^5x_s$ is valine Alternatively, a truncated peptide can be produced where a is present, with b and c also being present, to represent the original 12-mer; a is absent, with b and c being present, to represent an 11-mer; a and b are absent, with c only being present, to represent a 10-mer; a and b and c are absent, to represent a 9-mer as described above. The tryptophan and glycine residues may also be deleted resulting in the production of an 8-mer and 7-mer, respectively.

The three-letter and single-letter abbreviations for the amino acids are as follows:

Ala(A), alanine
Arg(R), arginine
Asn(N), asparagine
Asp(D), aspartic acid
Cys(C), cysteine
Gln(Q), glutamine
Glu(E), glutamic acid
Gly(G), glycine
His(H), histidine
Ile(I), isoleucine
Leu(L), leucine
Lys(K), lysine
Met(M), methionine
Phe(F), phenylalanine
Pro(P), proline
Ser(S), serine
Thr(T), threonine
Trp(W), tryptophan
Tyr(Y), tyrosine
Val(V), valine Description of Non-Human Primate and Human Clinical Subunit Vaccine Trials The only animal that can be reproducibly infected with HIV, thus providing an experimental system for testing the effectiveness of prototype vaccines, is the chimpanzee. Although chimpanzees can be experimentally infected with HIV-1, clinical disease has not, to date, developed in infected animals. Furthermore, the supply of chimpanzees available for biomedical research is limited since the assignation of the chimp as an endangered species. The recently described simian immunodeficiency virus (SIV, STLV-III), Desrosiers, R. C. and Letvin, N. L., *Rev. Infect. Dis.* (1987) 9:438–446, provides a potentially more useful model system based on the infection of rhesus macaques and African green monkeys (Kanki, et al., *Science* (1985) 230:951–1954).

SIV, although closely related to HIV-1 (Hirsch, et al., *Cell* (1987) 49:307–319; Franchini, et al., *Nature* (1987) 328:539–543; Chakrabarti, et al., *Nature* (1987) 328:543–547), is genetically more related to HIV-2 (Franchini, et al., supra, Chakrabarti, et al., supra), which also causes human AIDS (Clavel, et al., *N. Eng. J. Med.* (1987) 316:1180–1185). And, most importantly, SIV induces clinical AIDS similar to the human syndrome in infected macaques. (Desrosiers, R. C. and Letvin, N. L., supra).

The serologic diagnosis of SIV infection in monkeys has been made using traditional antibody assays, including enzyme-linked immunosorbent assay (ELISA) with whole-virus lysate as antigen. For the serologic diagnosis of HIV-1 infection in humans, a more sensitive, specific, as well as simple, diagnostic method has been investigated in ELISA systems using synthetic peptides as solid-phase antigens (site-directed ELISA). In particular, selected synthetic peptides that correspond to sequences from the amino-terminal half (amino acids 586–620) of the transmembrane glycoprotein (gp41) have reacted with over 99% of sera from human AIDS patients (Wang, et al., *Proc. Natl. Acad. Sci.* (U.S.A.) (1986) 83:6159–6163; Smith, et al., *J. Clin. Microbiol.* (1987) 25:1498–1504; Gnann, et al., *Science* (1987) 237:1346–1349; Gnann, et al., *J. Infect. Dis* (1987) 156:261–267; Chiodi, et al., *J. Med. Virol.* (1987) 23:1–9).

A synthetic peptide from an analogous region of the SIV transmembrane glycoprotein (gp32) is highly immunoreactive with sera from SIV-infected primates. This reactivity extends across four primate species from three genera and indicates infection by at least two distinct isolates of SIV in experimentally and naturally infected monkeys. (Johnson, et al., *AIDS Research and Human Retroviruses* (1988) 4:159–164.) Preliminary experiments also demonstrated that this peptide from the SIV gp32 reacted strongly with sera from humans infected with HIV-related West African viruses HIV-2 (HTLV-IV). Furthermore, reactivity with this peptide was specific for infection with the West African viruses, since these same sera did not react with the analogous peptides from HIV-1. (Norrby, et al., *Nature* (1987) 329:248–250.)

Sequences of the synthetic peptide used in the ELISA to detect antibodies against the SIV transmembrane glycoprotein (gp32) and the analogous regions from HIV-2 and HIV-1 are presented in FIG. 3, using the single-letter abbreviations for the amino acids. The sequences are numbered according to the Johnson reference, supra. It should be noted that the sequence for HIV-1 contains the 12 amino acid sequence of peptide 2 (amino acid residues 593–604 in the Franchini numbering system) described hereinafter in Example 8 and used in epitope mapping to determine the specificity for the human monoclonal antibody Anti-gp41 produced by Clone 3.

Non-identical amino acid residues for HIV-1 and HIV-2 compared with the analogous regions with the SIV sequence are denoted by double underlining. The two cysteine amino acid residues are marked by a singly underlined C.

The three analogous peptide sequences delineated above, consisting of 23 amino acid residues, have some unique biochemical structural features that are common to each. Two closely spaced cysteine residues may serve to orient the peptide in a similar configuration in order that an essential biological function can proceed, perhaps via disulfide bonding. The importance of these cysteine residues for maintaining antigenicity has been demonstrated recently for a similar HIV-1 peptide.

Sequential single amino acid deletions from the amino terminus of the 12 amino-acid peptide (amino acid residues 598–609 in the Gnann numbering system, which corresponds to amino acid residues 593–604 in the Franchini numbering system) of gp41 revealed a minor reduction in recognition by HIV-1 positive (polyclonal) sera in ELISA from 100% reactivity to 95%, 91%, and 86% activity when the amino acids leucine, glycine, and leucine, respectively, were specifically removed in a stepwise fashion.

Removal of the next two amino acid residues, tryptophan and glycine, which occupy analogous positions within both comparable epitopes for HIV-2 and SIV fitting the sequence formula tryptophan-glycine-cysteine-x-x-x-x-x-cysteine, produced eight and seven-residue oligopeptides (8-mer and 7-mer) that were reactive with only 64% and 48% of (polyclonal) sera from HIV-positive individuals, respectively. Thus, the essential epitope for immune recognition is determined as the 7-amino-acid sequence containing 2 cysteine residues (amino acids 603–609).

The smallest peptide retaining a degree of reactivity (with less than a 30% decrease in reactivity when compared to the original 12 amino acid sequence (12-mer)) was that structure with the common amino acid sequence tryptophan-glycine-cysteine-x-x-x-x-x-cysteine, or a nine amino acid peptide (9-mer). (Gnann, et al., *J. Virol.* (1987) 61:2639–2641).

Importantly, this region from HIV-1 is immunogenic as well as antigenic. Immunization of New Zealand white rabbits with the synthetic peptide leucine-glycine-leucine-tryptophan-glycine-cysteine-serine-glycine-lysine -leucine-isoleucine-cysteine (SEQ NO:28) (amino acid residues 598–609) induced high-titers of binding polyclonal antibodies. (Gnann, et al., *J. Infect. Dis.* (1987) 156:261–267.) No data characterizing biological function of the elicited antibodies were disclosed.

The unique and important characteristic of the described invention is that: a human B-lymphocyte cell line from an individual exposed to HIV-1 (naturally immunized by infection) has been established and immortalized, and is producing a biologically active fusion-blocking human monoclonal antibody directed against an epitope, within the peptide region described, that being specifically within the amino acid sequence leucine-glycine-isoleucine-tryptophan-glycine-cysteine-serine -glycine-lysine-leucine-isoleucine-cysteine (SEQ NO:2). This is believed to be the first report of human monoclonal antibodies that have been demonstrated to have fusion-blocking biological activity, as determined by syncytia inhibition assays, against HIV-1 gp41. Although other investigators have developed human monoclonal antibodies against gp41, these antibodies have no fusion-blocking biologic activity. (Banapour, et al., *J. Immunology* (1987) 139:4027–4033; Gorny, et al., *Pro. Natl. Acad. Sci.* (U.S.A.) (1989) 86:1624–1628; Kawamura, et al., V. International Conference on AIDS (1989), Abstract No. Th.C.O.4, p. 533; Boyer, et al., V. International Conference on AIDS (1989), Abstract No. T.C.P.59, p. 576; Zolla-Pazner, et al., V. Int'l Conf. on AIDS (1989), Abstract No. Th.C.O.10, p. 534).

Furthermore, computer modeling of the HIV-1 envelope protein sequence has predicted that the two amino acids (Ser-Gly) between the two cysteine residues in question participate in a β turn in the loop, hypothesized to be external to the viral membrane and formed by disulfide bonding between the two cysteines. (Johnson, et al, supra, p. 164, reporting on computer-modeling performed by Modrow, et al., *J. Virol.* (1987) 61:570–578). Thus, this region, which is also conserved among numerous isolates of HIV-1 (WMJ1, WMJ2, WMJ3, BH10, ARV2, LAV1A, HAT3), has distinctive biochemical and immunogenic structural properties that allow for a stable antigenic configuration, and, most importantly, also provides the essential biological fusion-associated function necessary for the virus to maintain infectiousness.

Specific Recommendation With Regard to Synthetic Peptide Selection As An Immunogen or Subunit Vaccine Trials The close resemblance of SIV (STLV-III) with HIV indicates that the further development of the experimental models first in rhesus macaques and African green monkeys will add a great deal to our knowledge in humans. The analogous 12 amino acid residue peptide (epitope) within the gp32 (SIV 617–628: LNAWGCAFRQVC) (SEQ NO:3) corresponds to both of the 12 amino acid residue peptides (or truncated peptides) within the gp41 immunodominant epitopes (HIV-1 593–604: LGIWGCSGKLIC (SEQ NO:2), a peptide whose biological function is essential for the maintenance of viral infectiousness (in the Gnann numbering system this peptide sequence is 598–609) and HIV-2 592–603: LNSWGCAFROVC) (SEQ NO:4) and could be utilized initially as a subunit vaccine component in an active immunization system in non-human primates. Model vaccine strategies could then be developed for application to a vaccine for human AIDS.

EXAMPLE 1

Production of Cell Lines Synthesizing Human Monoconal Antibodies to HIV

Peripheral blood, collected from a seropositive individual who had high titers of antibodies to HIV-1, was heparinized, centrifuged to remove plasma, then diluted 1:1 with phosphate buffered saline (PBS), pH 7.4, and subjected to Ficoll-Hypaque gradient centrifugation to obtain mononuclear cells. Approximately $1 \times 10^7$ mononuclear cells at the gradient interface were recovered, washed thrice with PBS and then incubated for 1.5 hours at 37° C. in 3 ml of filtered (0.45 micron) culture supernatant from EBV transformed marmoset cell line B95-8 containing 100,000 transforming units per ml. Cyclosporin A was then added at a final concentration of 2 micrograms/ml to inhibit suppressor T cells.

Lymphocytes were cultured in 1.5 ml of Iscove Modified Dulbecco's Medium (Iscove, N. N. and Melchers, F., *J. Exp. Med.* (1978) 147:923–928) supplemented with 10% (vol/vol) fetal bovine serum (HyClone), L-glutamine (2 mM), penicillin (100 units/ml), streptomycin (100 micrograms/ml), and fungizone (0.25 micrograms/ml) media for 3 weeks in 24 well plates (Costar) at a concentration of $1 \times 10^6$ cells/ml, in an atmosphere of 5% carbon dioxide at 37° C.

After screening for anti-HIV antibody production by a commercial Enzyme-linked Immunosorbent Assay (ELISA) (Genetic Systems, Seattle, Wash.), positive culture wells were cloned by limiting dilution in 96-well, U-bottom plates at 1 cell per well on a feeder layer of irradiated (3000R) human lymphocytes (20,000 cells/well).

An aliquot of lymphoblastoid cells testing positive for anti-HIV production was expanded in 25 cm² flasks, 7 ml/flask, (Costar) and cultured for an additional week to a concentration of approximately $1 \times 10^6$ cells/ml. Lymphoblastoid cells were then fused by polyethylene glycol (PEG 50%, MW 1000) with heteromyelomas (HAT sensitive, resistant) in a ratio of 2:1 for preparation of hybridomas. (Bartal, A. H. and Hirshaut, Y. *Methods of Hybridoma Formation* (1987)).

Cell lines with supernatants testing positive for anti-HIV antibodies were then subcloned twice by limiting dilution at 0.3 cells per well in 96-well, U-bottom microtiter plates, to assure monoclonality of the produced antibody. Each cell line has been cryopreserved in liquid nitrogen to form a master cell bank (MCB). The cells were frozen at a concentration of $5 \times 10^6$ cells/ml in a freezing solution of Iscove media supplemented with 20% fetal bovine serum and 10% dimethylsulfoxide, 1 ml/ampule.

EXAMPLE 2

Human Monoclonal Antibody Screening By Enzyme-Linked Immunosorbent Assays (ELISA) Supernatants from culture wells demonstrating cell growth were assayed for the presence of human anti-HIV antibodies using commercially prepared ELISA plates coated with whole-viral (LAV= lymphadenopathy virus) lysates (e.g., those produced by Genetic Systems, Seattle, Wash.) and envelope glycoprotein, specifically gp160 (e.g., those produced by MicroGeneSys, West Haven, Conn.) as target antigens. The human monoclonal antibody (produced by Clone 3, ATCC No. ATCC CRL 10198) reacts with the envelope (env) gene encoded protein gp160 in ELISA testing, and more specifically gp41, the transmembrane glycoprotein envelope component and is designated Anti-gp41. The specificity was determined using the recombinant peptide 121 (p121) as the target antigen in ELISA testing. The p121 is a polypeptide that contains about one-half of the gp41 sequence (the amino terminal half), a major portion of the immunodominant epitopes. (Chang, et al., *Bio/Technology* (1985) 3:905–999). The human monoclonal antibody does not reacts with gp120 when tested in a parallel ELISA method against the (external) surface envelope glycoprotein. The specificity results are set forth in Table 1 below. FIG. 4 depicts a linear comparison of the peptide sequences tested.

TABLE ONE

Specificity of Human Monoclonal Antibody ANTI-gp41 Determined by ELISA

|  | gp160 | gp120 | p121 | 12-mer* | no Ag |
|---|---|---|---|---|---|
| Human Monoclonal Antibody | + | − | + | + | − |
| Donor Patient Serum | + | NT | NT | + | − |
| Normal Human Serum | − | NT | NT | − | − | gp160 = envelope glycoprotein precursor . . . (856 amino acids #001–856)
gp120 = surface envelope glycoprotein . . . (518 amino acids #001–518)
gp41 = transmembrane envelope glyprotein . . . (338 amino acids #519–856)
p121 = recombinant peptide, within gp41 sequence . . . (082 amino acids #565–646)
12-mer = conserved 12 amino acid peptide, within gp41 sequence . . . (012 amino acids #598–609)
no Ag = no antigen
+ = positive reaction; mean optical density (O.D.) of test greater than mean O.D. of negative control plus twice the standard deviation. (Barnett, 1979, Clin. Lab. Stat., p 124, Little)
− = negative reaction; mean optical density (O.D.) of test less than mean O.D. of negative control plus twice the standard deviation.
*leucine-glycine-isoleucine-tryptophan-glycine-cysteine-serine-glycine-lysine-leucine-isoleucine-cysteine (Seq. No. 2)
NT = not tested

EXAMPLE 3

Immunoblotting

Figure 1:
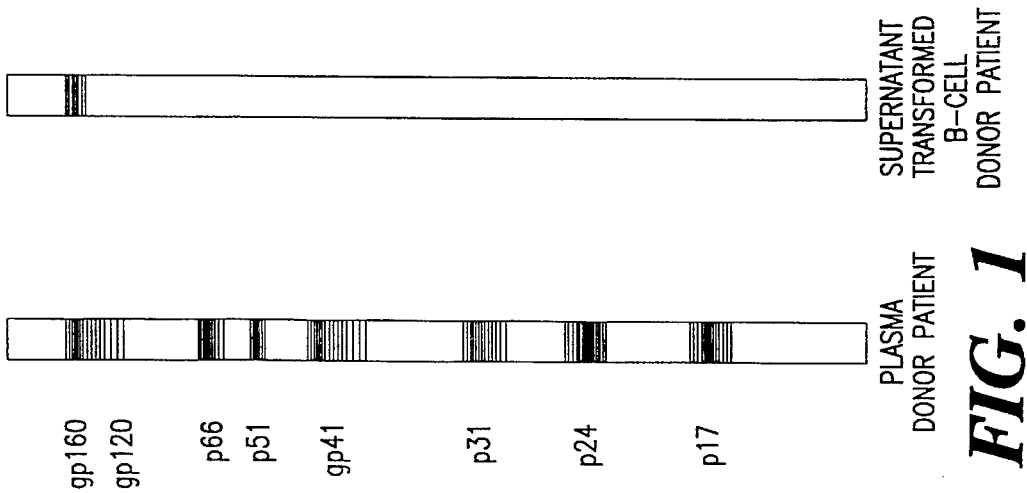

Additional analyses of specificity were carried out by Western blot (WB) with Biotech Research Labs (Rockville, Md.) and Immunetics (Cambridge, Mass.) HIV-antigen preblotted nitrocellulose membranes using standard techniques. The human monoclonal antibody reacts with an HIV-1 major antigen component of 160 kilodaltons (kDa) in viral lysates. It has been determined that noncovalently associated tetramers of gp41 represent the native form of the transmembrane glycoprotein in virions, and that monoclonal antibodies preferentially recognize the oligomeric complexes over monomeric gp41 in Western blots (Pinter, et al., *J. Virol.* (1989) 63:2674–2679). FIG. 1 depicts the Western blot testing of the donor patient plasma and the supernatant from the transformed human B cell line using Biotech Research Labs HIV-antigen preblotted nitrocellulose membranes. The results demonstrate a positive reaction for the supernatant corresponding to a band at 160 kDa and co-migrating with gp160.

EXAMPLE 4

Immunoblotting Under Reducing Conditions

Figure 8:
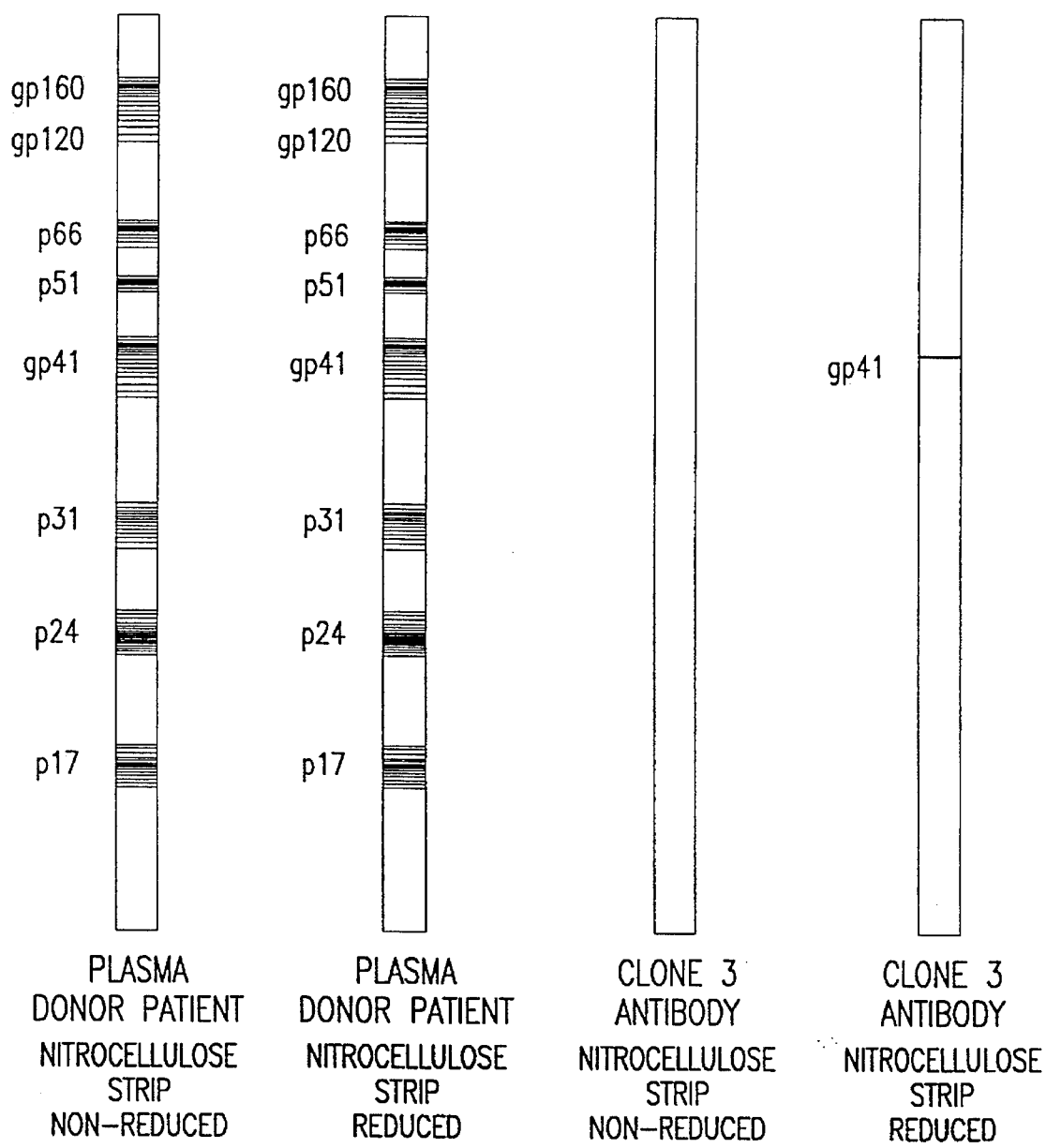
Figure 9:
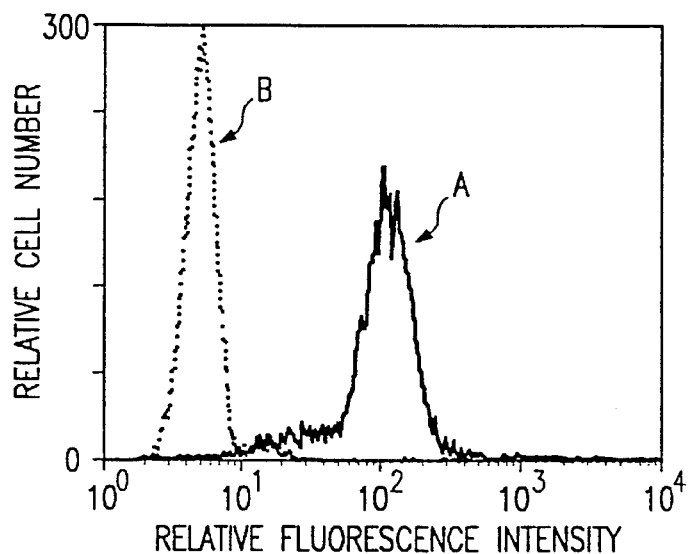

FIG. 8 represents the Western blot (WB) testing of the donor patient plasma and the affinity-chromatography purified IgG human monoclonal Anti-gp41 antibody (Clone 3 Antibody) using Immunetics (Cambridge, Mass.) HIV-antigen preblotted nitrocellulose membranes.

In order to reduce disulfide bridges (both intermolecular and intramolecular) that might have formed due to the two invariant cysteine residues, contained within the gp41, mediating the formation of oligomers or cyclic antigenic conformations (reference: Berman, P. W., et al., *Journal of Viroloy*, August 1989 63:(8), pp. 3489–3498, Expression and Immunogenicity of the Extracellular Domain of the Human Immunodeficiency Virus Type 1 Envelope Glycoprotein, gp160) the commercially obtained (Immunetics) HIV-antigen preblotted nitrocellulose strips were prepared, immediately prior to utilization, with the following modification of the standard procedure described below:

The HIV-antigen preblotted nitrocellulose strips were incubated in PBS buffer, pH 7.4, with β-mercaptoethanol (1% volume/volume), a reducing agent, at either 37° C. for two hours or 95° C. for two minutes.

Standard immunoblotting technique was then carried out for testing of the samples described above, utilizing both reduced and non-reduced preblotted nitrocellulose strips, in a parallel procedure.

The significant results demonstrated a (weak) positive reaction for the human monoclonal antibody (Clone 3 Antibody) corresponding to a band at 41 kDa and co-migrating with gp41 only when the HIV-antigen preblotted nitrocellulose strip has been reacted with the reducing agent β-mercaptoethanol. No corresponding reaction band was noted between the human monoclonal antibody (Clone 3 Antibody) and the HIV-antigen migrating at 41 kDa when the HIV antigen preblotted nitrocellulose strip was not subjected to pretesting reduction treatment with β-mercaptoethanol.

These data indicate that the human monoclonal antibody (Clone 3 Antibody) reacted preferentially with the reduced (linear) gp41 fusion-associated octapeptide epitope, GCS-GKLIC (SEQ NO:1), in immunoblotting.

EXAMPLE 5

Affinity Chromatography Isolation and Purification of Human Monoclonal IgG

Aliquots (500 ml volumes) of hybridoma cell culture supernatants (spent cell culture media) were subjected to batch immunoadsorption utilizing Sepharose® 4-Fast Flow coupled protein G (Pharmacia, Piscataway, N.J.), a recombinant streptococcal IgG Fc receptor, that has the capacity of adsorbing 17 mg of human IgG (all subclasses) per ml of gel. The immunoadsorbed monoclonal antibody was eluted from the matrix via low pH buffer (0.1M glycine-HCl, pH 2.4) with rapid neutralization of eluate by collection into 1.0M TRIS-HCl buffer (pH 9.0) for a final pH of 7.8.

EXAMPLE 6

Determination of Immunoglobulin Class and Subclass

The class and light-chain type of Anti-gp41 monoclonal antibody were determined by ELISA. For these assays, commercially-prepared microtiter plates coated with gp160 (MicroGeneSys) were incubated with culture supernatants (or purified human monoclonal anti-gp41 IgG). The type (class) of antibody was determined with the following horseradish peroxidase-coupled antibodies: goat anti-human IgG (γ chain specific) and goat anti-human IgM (μ chain specific) (Zymed Laboratories, San Francisco, Calif.). The subclass of the human monoclonal antibody was also analyzed by ELISA with horseradish peroxidase conjugated mouse monoclonal antibodies against the four subclasses (IgG1, IgG2, IgG3, IgG4) of human IgG (Zymed Laboratories, San Francisco, Calif.). The light-chain type of Anti-gp41 was determined by exclusion using peroxidase-labeled mouse monoclonal antibody anti-human κ chain. The immunological characterization data of the human monoclonal antibody (Anti-gp41) indicated that the immunoglobulin was of the IgG class, specifically subclass 1, with non-κ, therefore probably λ, light-chain determinants.

In an additional immunologic study, in a dot-immunobinding assay (DIBA) on nitrocellulose membranes, as described by Jol-Van der Zijde, et al., *Journal of Immunological Methods* (1988) 108:195–203, the human monoclonal antibody (Clone 3 Antibody) was demonstrated to react with antiserum (Zymed Laboratories, San Francisco, Calif.) monospecifically directed against the λ light-chain.

EXAMPLE 7

Quantitation of Anti-gp41 Human Monoclonal IgG1

IgG quantitation was performed on affinity purified protein by the Lowry technique using purified protein (albumin) to produce the standard curves used in calculations. (Lowry, et al., *J. Biol. Chem.* (1951) 193:265). The concentration of IgG produced by the cell lines varied, but generally reached a maximum at day 9 of culture, ranging from 2–10 micrograms/ml.

EXAMPLE 8

Epitope Mapping of Human IgG1 Monoclonal Anti-gp 41 Antibody Binding to Transmembrane Glycoprotein gp41

The wells of Immulon II microELISA plates (Dynatech Industries, McLean, Va.) were coated for a minimum of 12 hours at 4° C. with a solution of the synthetic peptide 2, leucine-glycine-isoleucine-tryptophan-glycine-cysteine-serine-glycine-lysine-leucine-isoleucine-cysteine (SEQ NO:2) (Cambridge Research Biochemicals, Valley Stream, N.Y.). The peptide was solubilized initially with 10% acetic acid and then brought to a final concentration of 10 μg/ml, pH 6.4 in PBS. One hundred microliters of this solution was added per well. In order to minimize polymerization, β-mercaptoethanol (0.5% vol/vol) was added to the solution. The wells were emptied of peptide solution, washed thrice with 300 microliters PBS containing 0.05% polyoxyethylene (20) sorbitan monolaurate (e.g., Tween 20, produced by ICI Specialty Chemicals) then twice with 300 microliters of PBS alone. Excess binding sites were blocked (quenched) with 200 microliters of PBS containing 1% bovine serum albumin (BSA) per well. Wells containing no peptide were subjected to the blocking process to be utilized as one parameter of negative controls. The wells were incubated with the blocking solution for 3 hours at room temperature, then emptied by aspiration, and washed thrice with 300 microliters of PBS. The wells were emptied, dried and the peptide-coated plates were then stored with desiccant in a sealed bag at 4° C. The peptide-coated plates are stable for at least 3 months when stored in this manner.

To test the binding characteristics of the human monoclonal Anti-gp41 antibody with the synthetic peptide, affinity-chromatography purified IgG (700 micrograms/ml) was serially diluted in PBS with 0.05% polyoxyethylene (20) sorbitan monolaurate and 1% BSA and reacted (100 microliters) in the peptide-coated wells and in wells without antigen (negative control) for 2 hours at 37° C. Normal human serum (negative control) and the donor patient serum were diluted 1:401 and reacted in the ELISA test against the peptide-coated wells and in wells without antigen (negative control). After the initial incubation period, the test samples and controls were aspirated from the wells which were then washed 9 times with 300 microliters of 0.05% polyoxyethylene (20) sorbitan monolaurate in PBS. A solution of 100 microliters of goat anti-human IgG conjugated to horseradish peroxidase was diluted 1:100 and added to the wells. After 2 hours at 37° C., the wells were washed again with 0.05% polyoxyethylene (20) sorbitan monolaurate in PBS, 9 times, and then incubated with 100 microliters of tetramethyl-benzidine chromogen in dimethylsulfoxide (DMSO) with buffered hydrogen peroxide substrate for 30 minutes at room temperature. The reaction was stopped by the addition of 100 microliters of 1N sulfuric acid ($H_2SO_4$) and the optical density or absorbance of the solution determined at 490 nm, a colorimetric determination in the visible spectrum.

The results indicate that the human monoclonal antibody binds specifically to the gp41 peptide with the amino acid sequence leucine-glycine-isoleucine-tryptophan-glycine-cysteine-serine-glycine-lysine-leucine-isoleucine-cysteine (SEQ NO: 2), as did the patient serum. Normal human serum controls were negative. Additionally, the human monoclonal antibody, patient serum, and normal human serum did not bind to uncoated (no antigen) wells of the Immulon II ELISA plate. (See Table 1).

EXAMPLE 9

Epitome Mapping of Human IgG1 Monoclonal Anti-gp41 Antibody Binding to Transmembrane Glycoprotein gp41

The biochemically and immunologically defined human monoclonal antibody is produced by the Clone 3 cell line (ATCC CRL 10198) and is directed against the HIV-1 transmembrane glycoprotein gp41, specifically the 12 amino acid peptide (12-mer=Peptide 2), Leu-Gly-Ile-Trp-Gly-Cys-Ser-Gly-Lys-leu-Ile-Cys (SEQ NO:2) (Example 8, Table 1), which has two potential antibody binding regions (epitopes).

Others (Mathiesen, et al., *Immunology* (1989) 67:1–7) have recently investigated the binding capacity only of polyolonal human IgG antibody with two overlapping HIV-1 gp41 peptides (E34/E32; amino acid positions 587–608 and 600–618) in order to define the amino acids involved in epitopes and antibodies interactions.

The IgG paratopes showed reactivity to two regions (Mathiesen, id.: page 3, first column; page 4, Table 3) within the Peptide 2 sequence, Leu-Gly-Ile-Trp-Gly-Cys-Ser-Gly-Lys-Leu-Ile-Cys, (SEQ NO:29) under consideration in this patent. The two paratopes reacted with the regions within the Peptide 2 sequence consisting of the amino acid sequences Ile-Trp-Gly and Gly-Cys-Ser-Gly-Lys-Leu-Ile-Cys (SEQ NO:1).

Figure 6:
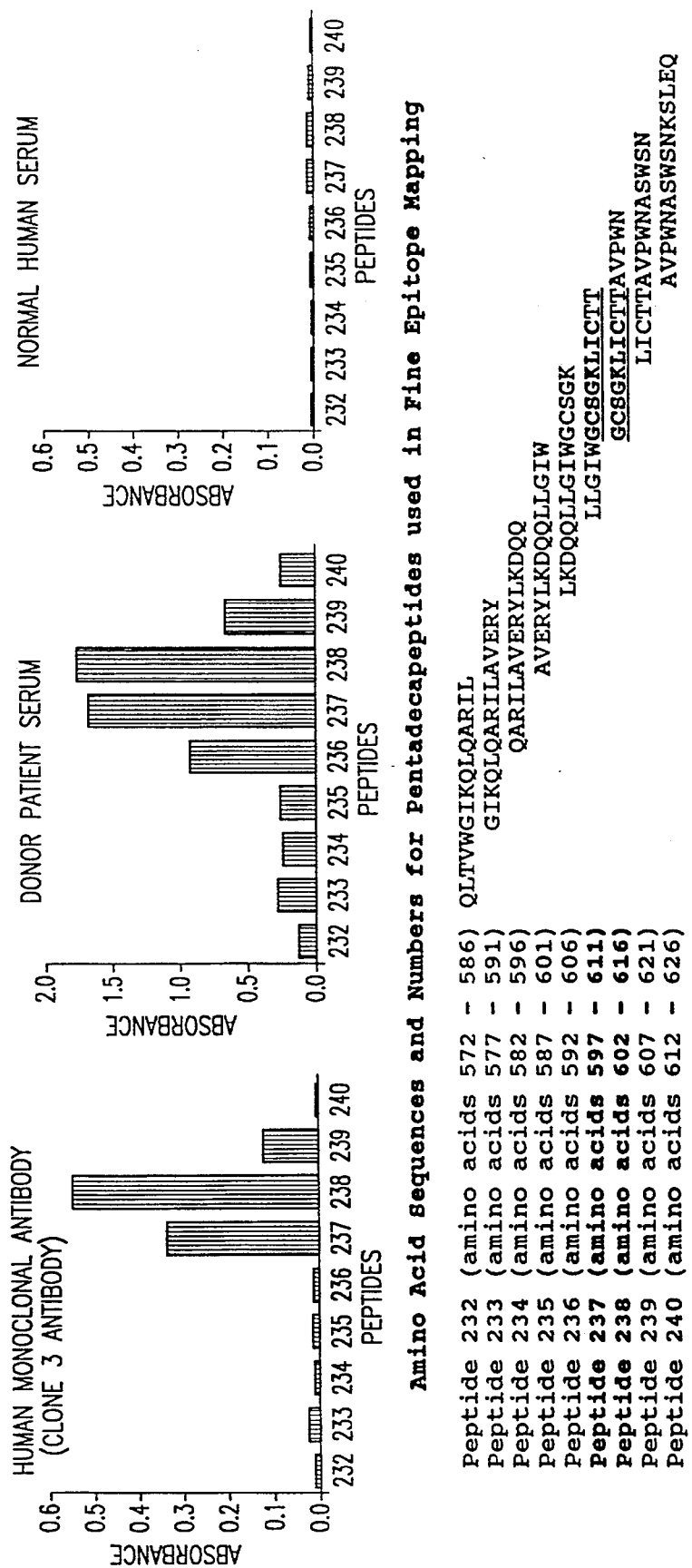

As shown below in Example 9, Table Two, FIG. 5; Example 10, Table Three, FIG. 6 and FIG. 7, the human monoclonal antibody (Clone 3 antibody) binds preferentially to at least a portion of the amino acid sequence Gly-Cys-Ser-Gly-Lys-Leu-Ile-Cys (SEQ NO:1), an octapeptide (8-mer) which contains only one complete epitope of the two antibody binding regions within the 12-mer.

The interaction of the fusion blocking human monoclonal antibody with the identified structural octapeptide sequence (8-mer) (Example 9, Table Two, FIG. 5) thereby ascribes for the first time an associated neutralizable physiological function to the immunogenic octapeptide epitope, that being fusion-associated function.

The biological function of the delineated single epitope, consisting of the octapeptide amino acid sequence Gly-Cys-Ser-ely-Lys-Leu-Ile-Cys (SEQ NO:1) (8-met), denoted as fusion-associated epitope, is not known to have been described previously in any published or presented scientific paper. These data are presented in Examples 11 and 18 herein.

The wells of Immulon II microELISA plates (Dynatech Industries, McLean, Va.) were coated for a minimum of 12 hours at 4° C. with a solution of the synthetic peptide 6120 (linear), glycine-cysteine-serine-glycine-lysine-leucine-isoleucine-cysteine-threonine-threonine-alanine-valine-proline-tryptophan-asparagine-alanine-serine (SEQ NO:5). The cyclic peptide 6120 (IAF BioChem International, Inc., Montreal, Canada) was solubilized initially with 10% acetic acid and then brought to a final concentration of 10 micrograms/ml, pH 6.4 in PBS. In order to minimize polymerization and cyclization and to reduce the cyclic peptide, β-mercaptoethanol (1% vol/vol) was incubated with the solution for 1 hour at 37° C. Then, one hundred microliters of this reduced, linear peptide solution was added per well. The wells were emptied of peptide solution, washed thrice with 300 microliters PBS containing 0.05% polyoxyethylene (20) sorbitan monolaurate (e.g., Tween 20, produced by ICI Specialty Chemicals) then twice with 300 microliters of PBS alone. Excess binding sites were blocked (quenched) with 200 microliters of PBS containing 1% bovine serum albumin (BSA) per well. Wells containing no peptide were subjected to the blocking process to be utilized as one parameter of negative controls. The wells were incubated with the blocking solution for 3 hours at room temperature, then emptied by aspiration, and washed thrice with 300 microliters of PBS. The wells were emptied, dried and the peptide-coated plates were then stored with desiccant in a sealed bag at 4° C. The peptide-coated plates were stable for at least 3 months when stored in this manner.

To test the binding characteristics of the human monoclonal Anti-gp41 antibody with the synthetic peptide 6120, affinity-chromatography purified IgG, (1 mg/ml) was serially diluted in PBS with 0.05% polyoxyethylene (20) sorbitan monolaurate and 1% BSA and reacted (100 microliters) in the peptide-coated wells and in wells without antigen (negative control) for 2 hours at 37° C. Normal human serum (negative control) and the donor patient serum were diluted 1:401 and reacted in the ELISA test against the peptide-coated wells and in wells without antigen (negative control). After the initial incubation period, the test samples and controls were aspirated from the wells which were then washed 9 times with 300 microliters of 0.05% polyoxyethylene (20) sorbitan monolaurate in PBS. A Solution of 100 microliters of goat anti-human IgG conjugated to horseradish peroxidase was diluted 1:100 and added to the wells. After 2 hours at 37° C., the wells were washed again with 0.05% polyoxyethylene (20) sorbitan monolaurate in PBS, 9 times, and then incubated with 100 microliters of tetramethyl-benzidine chromogen in dimethylsulfoxide (DMSO) with buffered hydrogen peroxide substrate for 30 minutes at room temperature. The reaction was stopped by the addition of 100 microliters of 1N sulfuric acid ($H_2SO_4$) and the optical density or absorbance of the solution determined at 490 nm, a colorimetric determination in the visible spectrum.

The results indicate that the human monoclonal antibody (Clone 3 Antibody) binds specifically to the gp41 peptide with the amino acid sequence glycine-cysteine-serine-glycine-lysine-leucine-isoleucine-cysteine -threonine-threonine-alanine-valine-proline-tryptophan-asparagine-alanine-serine (SEQ NO:5) (reduced, linear, non cyclic), as did the donor patient serum. Normal human serum controls were negative. (Table Two).

The amino acid sequence common to both Peptide 2 (12-mer) and Peptide 6120 and to which Clone 3 human monoclonal antibody binds is the octapeptide (8-mer) glycine-cysteine-serine-glycine-lysine-leucine-isoleucine-cysteine (SEQ NO:1). (See FIG. 5).

TABLE TWO

Specificity of Human Monoclonal Antibody
(Clone 3 Antibody)
ANTI-gp41
Determined by ELISA

|  | Peptide 2* (12-mer) | Peptide 6120 | no Ag |
|---|---|---|---|
| Human Monoclonal Antibody | + | + | − |

TABLE THREE

Specificity of Human Monoclonal Antibody
(Clone 3 Antibody)
ANTI-gp41
Determined by ELISA

|  | Peptide 235 | Peptide 236 | Peptide 237 | Peptide 238 | Peptide 239 | Peptide 240 |
|---|---|---|---|---|---|---|
| Human Monoclonal Antibody | 0.01* | 0.01 | 0.33 | 0.56 | 0.12 | 0 |
| Donor Patient Serum | 0.25 | 1.00 | 1.70 | 1.75 | 0.70 | 0.25 |
| Normal Human Serum | 0 | 0 | 0 | 0 | 0 | 0 |

Sera samples diluted 1:50; human monoclonal antibody concentration = 20 µg/ml)
Peptide 235 = (15 amino acids #587–601)    AVERYLKDQQLLGIW (Seq. No. 6)
Peptide 236 = (15 amino acids #592–606)    LKDQQLLGIWGCSGK (Seq. No. 7)
Peptide 237 = (15 amino acids #597–611)    LLGIWGCSGKLICTT (Seq. No. 8)
Peptide 238 = (15 amino acids #602–616)    GCSGKLICTTAVPWN (Seq. No. 9)
Peptide 239 = (15 amino acids #607–621)    LICTTAVPWNASWSN (Seq. No. 10)
Peptide 240 = (15 amino acids #612–626)    AVPWNASWSNKSLEQ (Seq. No. 11)
*Absorbance = Optical Density (OD) at 490 nm
The decapeptide amino acid sequence common to both Peptide 237 and Peptide 238, the peptides for which the Human Monoclonal Antibody (Clone 3 Antibody) had the greatest binding, is underscored.
The fusion-associated epitope, GCSGKLIC, is an octapeptide contained within the decapeptide.

TABLE TWO-continued

| Donor Patient Serum | + | + | − |
|---|---|---|---|
| Normal Human Serum | − | − | − |

*Peptide 2(12-mer) = 12 amino acid peptide within gp41 sequence . . . (amino acids #598–609)
Peptide 6120 = 17 amino acid peptide with gp41 sequence . . . (amino acids #602–618)
no Ag = no antigen
+ = positive reaction; mean optical density (O.D.) of test greater than mean O.D. of negative control plus twice the standard deviation. (Barnett, 1979, Clin. Lab. Stat., p. 124, Little)
− = negative reaction; mean optical density (O.D.) of test less than mean O.D. of negative control plus twice the standard deviation.

EXAMPLE 10

Fine Epitope Mapping of Human IgG1 Monoclonal Anti-gp41 Antibody by ELISA Using Synthetic Pentadecapeptides (15 Amino Acid Peptides)

Pentadecapeptides, sequentially overlapping by 10 amino acids were synthesized on the basis of HTLV-IIIB, clone B10 (Ratner et al., Nature (1985) 313:277), for gp41 peptides 232–240 (amino acids 572–626). These were synthesized according to the solid-phase method of Merrifield, J. Amer. Chem. Soc. (1963) 85:2149, modified by Houghten, Proc. Natl. Acad. Sci. U.S.A. (1985) 82:5131. For human monoclonal antibody ELISAs, microwell plates (Nunc Immunoplate I) were coated with 1 microgram of peptide/microwell. Sera samples and affinity column (Protein G) purified human monoclonal antibody were assayed in dilutions of 1:50 for 105 minutes at 37° C. Mouse antibodies to IgG were used to bind to human IgG and subsequently detected by HRPO-conjugated anti-mouse Ig. A color reaction was obtained with ortho-phenylenediamine (OPD) and the optical density (OD) at 490 nm was recorded. Blanks and HIV seronegative controls were included in all plates. Sera and human monoclonal antibody giving greater than 3 times the mean OD of negative controls (always more than mean+ 3SD) were scored as positive for IgG and peptide.

The results indicate that the human monoclonal antibody (Clone 3 Antibody) binds specifically to Peptide 237 and Peptide 238, as did the donor patient serum. Normal human serum controls were negative. (Table Three and FIG. 6). The decapeptide sequence common to both Peptide 237 and Peptide 238 contains the octapeptide amino acid sequence, the fusion-associated epitope (FIG. 7).

The biological reactivity of the human monoclonal antibody (Clone 3 Antibody) has been demonstrated in inhibition of syncytia formation assays wherein the neutralization capacity of the human monoclonal antibody is characterized by the blocking of fusion between HIV-1 infected and uninfected human cells (Example 11, Table Four, FIG. 2) and by neutralization of free HIV-1 (SF2) infectivity as presented below in Example 18 and Table Five.

EXAMPLE 11

Quantitative Synctium-Forming Microassay for the Detection of Human Immunodeficiency Virus Neutralizing Antibody Traditionally, retroviruses, including HIV-1, can be assayed directly by a number of simple focus-forming or syncytium-forming assays. (Nara, et al., *AIDS Research and Human Retroviruses* (1987) 3:283–302; Putney, et al., *Science* (1986) 234:1392–1395). These assays are very sensitive, simple, relatively rapid, and allow for ready biological assessment concerning infectivity of virus under various in vitro conditions. Additionally, various virus-envelope associated properties such as interference by inhibitory agents or neutralization by antibodies can be studied.

The human monoclonal antibody anti-gp41 was tested in the syncytium-forming microassay procedure, as described by Putney, to ascertain HIV-1 neutralization capabilities as demonstrated by fusion inhibition. The microtiter syncytium-forming assay utilized a clone of CEM (CD4+) cells chronically infected with the HIV-1 isolate HTLV-IIIB, and MOLT-4 (CD4+) cells. CEM cell stocks stably infected with HTLV-IIIB, yet not susceptible to the cytopathological effects of the virus, were used as the infected partner and MOLT-4 cells were used as the uninfected partner. Cells were washed once in growth media and cell concentrations were adjusted to $0.125\times10^6$ cells/ml and $1.75\times10^6$ cells/ml for CEM and MOLT-4 cells, respectively. Ninety-six well, half-area plates were used in the assay. Anti-gp41 antibody solution was added to half-area wells in a volume of 10–20 microliters. Forty microliters of each cell solution was then added to the well, resulting in a ratio of approximately 5,000 HTLV-IIIB-infected CEM cells to 70,000 uninfected MOLT-4 cells per well. Plates were incubated at 37° C. in an atmosphere of 5% $CO_2$ for 20–24 hours.

Syncytia formation of cells, or giant cell formation, was enumerated using an inverted microscope at 40× magnification. The number of giant cells, defined as multinucleated fused cells being 5 times the diameter of input cells, were scored as the number of syncytium-forming units per well.

The results of fusion inhibition by Anti-gp41 are quantitatively reported. The human monoclonal antibody concentration with the corresponding syncytium-forming units (SFUs) observed are presented in Table Four below, where $V_o$ is the total number of virus induced SFUs per well in the absence of antibody and $V_n$ is the number of SFUs per well in the presence of antibody, in doubling dilutions of (decreasing concentration).

TABLE FOUR

| Syncytium-Forming Microassay | |
| --- | --- |
| HUMAN Monoclonal Antibody* Dilution | Number of Syncytium-Forming Units (SFU) $V_n$ |
| 1:5 (140 μg/ml) | 6 |
| 1:10 (70 μg/ml) | 22 |
| 1:20 (35 μg/ml) | 35 |
| 1:40 (17.5 μg/ml) | 39 |
| 1:80 (8.75 μg/ml) | 33 |
| Control (no antibody) ($V_o$) | 36 |

SFU average of replicates of quadruplicate determinations ($V_n$ and $V_o$)
*700 micrograms/ml = (protein concentration neat)

The human monoclonal Anti-gp41 antibody at a 1:5 dilution (the minimum dilution allowed and therefore the maximum antibody concentration tested in the microassay system) decreased in number the formation of syncytium-forming units between HIV-1 (HTLV-IIIB) infected CD4+ cells and uninfected target CD4+ (MOLT-4) cells from 36 ($V_o$) to 6 ($V_n$) for a fusion inhibition of 83%. Replicate tests were performed in quadruplicates, and fusion inhibition percentage values were calculated from the reduction in virus-induced, syncytial-forming units, represented as ($V_o$-$V_n$), obtained in the presence of two-fold dilutions of human monoclonal Anti-gp41, divided by the number of total virus induced SFUs added ($V_o$).

In the microassay system, the concentration of the affinity column (Protein G) purified human monoclonal Anti-gp41 IgG1 that resulted in an 83% inhibition in syncytium-formation was 140 micrograms/ml, a physiological concentration. The 50% SFU inhibition point ($V_n$=18) was obtained at a human monoclonal Anti-gp41 IgG1 antibody concentration of ~88 micrograms/ml. (See FIG. 2).

EXAMPLE 12

Therapeutic Uses For Anti-gp41

The antibody of the invention may be used therapeutically, as described below, in the modality of passive immunotherapy. Human monoclonal antibodies with the proper biological properties are useful directly as therapeutic agents. Data to support the efficacy and delineation of the therapeutic protocols for passive immunotherapy in other primates (chimpanzees) have been published, for it has been determined that neutralization of in vivo HIV-1 infectivity can be mediated by in vitro neutralizing antibody directed against the hypervariable loop of the viral envelope (gp120). Chimpanzee-derived polyclonal antibodies were utilized in the protocol. (Emini, et al., V. International Conference on AIDS (1989), Abstract No. Th.C.O.30, p. 538). By administering an appropriate human monoclonal antibody to patients who lack neutralizing antibodies against the envelope epitope within gp41, passive immunotherapy can be provided.

In a parallel human study, data from recent clinical trials (Jackson, et al., *Lancet* (1988) 2:647–652; Karpas, A., *Proc. Natl. Acad. of Sciences (U.S.A.)* (1988) 85:9234–9237) have demonstrated that passive immunization improved the status of patients with advanced (symptomatic) AIDS. In those trials passive immunization was accomplished by transfusing plasmas containing antibodies from asymptomatic AIDS patients into the symptomatic AIDS recipients.

For example, the passive immunization method against hepatitis B virus has been utilized in humans, when clinically indicated, as routine effective measures of post-viral exposure prophylaxis, wherein hepatitis B immune globulin is administered to the at-risk recipient at a dose of 0.06 ml/kg IM (Center for Disease Control, Department of Health and Human Services. "Recommendations for Protection Against Viral Hepatitis. Recommendation of the Immunization Practices Advisory Committee." *MMWR* (1990) 39:1–26).

When a neutralizing agent, such as a human monoclonal antibody, is used in passive immunotherapy, the protocol regimen can parallel that for the administration of hepatitis B immune globulin (e.g., H-BIG®, a solution of human immunoglobulin obtained from pooled venous plasma of individuals with high titers of antibody to the hepatitis B surface antigen, prepared by Abbott Laboratories, North Chicago, Ill. 60064).

Neutralizing antibodies and antibodies mediating antibody-dependent cellular cytotoxicity (ADCC) to HIV represent important responses sought (for effective passive immunotherapy and) in an effective HIV vaccine for active immunization. (Weiss, et al., *Nature* (1985) 316:69–71; Robert-Guroff, et al., supra, 72; Ho, et al., *J. Virol.* (1987) 61:2024; Cheng-Mayer, et al., *Proc. Natl. Acad. Sci. (U.S.A.)* (1988) 85:2815; and Rook, et al., *J. Immunol.* (1987) 138: 1064; Ljunggren, et al., (1987) 139:2263; Ojo-Amaize, et al., 2458; Blumberg, et al., *J. Infect. Dis.* (1987) 156:878; Shepp, et al., id. (1988) 157:1260; Tyler, et al., V International Conference on AIDS (1989), Abstract No. T.C.O.33, p. 521).

It is significant, therefore, that Clone 3 Antibody, which binds to the gp41 fusion-associated epitope (GCSGKLIC) (SEQ NO:1), can both prevent fusion of virus-infected cells and neutralize infectivity of free virus particles, as demonstrated by biological assays presented in Example 11 and Example 18, respectively.

Alternatively, the monoclonal antibody can be bound to a toxin such as deglycosylated ricin A (dgA) chain to form an immunotoxin (IT). Methods for producing immunotoxins of antibodies are well known. The A chain of ricin may be chemically deglycosylated to prevent any immunotoxin subsequently formed from binding to the parenchymal and nonparenchymal cells of the liver through mannose receptors. To produce the derivatized antibody which can then be coupled to dgA, N-succinimidyl 3-(2-pyridyldithio) propionate dissolved in dimethyl-formamide may be added to a solution of the antibody (5 mg/ml) in 0.1M sodium phosphate buffer with 0.003M $Na_2$ EDTA (disodium ethylenediamine tetracetic acid) (pH 7.5) to a final concentration of 1 mM. After 30 minutes at room temperature, the solution may be desalted on a column of Sephadex G-25. The derivatized immunoglobulin may then be added to the dgA chain solution at a ratio of 1.3 mg of deglycosylated A chain to 1 mg of IgG and maintained for 2 hours at 25° C., followed by overnight at 4° C. The resultant IT-dgA (immunotoxin dgA chain-antibody) may then be purified on Sephacryl ACA-44. (Till, et al., *Proc. Natl. Acad. Sci.* (U.S.A.) (1989) 86:1987–1991).

Only HIV-1-infected cells express viral proteins on their surface. Consequently, only those cells infected with the virus will express gp41. Since the monoclonal antibody of this invention binds to gp41, the monoclonal antibody will be able to target the toxin to only those cells infected with the virus. Additionally, gp41 is a highly conserved peptide, thereby making the therapy described practicable. This particular monoclonal antibody is also able to inhibit cellular fusion between HIV-1-infected and uninfected cells, thus effecting dual purposes when conjugated to the deglycosylated ricin A chain.

Also included within the scope of the invention are useful binding fragments of the described monoclonal antibody, such as Fab, F(ab')$_2$, and Fv fragments. The antibody fragments are obtained by conventional techniques. Useful binding fragments may be prepared by peptidase digestion of the antibody using papain or pepsin. Consequently, the antibodies, or fragments thereof, may be injected either with or without a conjugated material for use in treating individuals already infected with AIDS.

EXAMPLE 13

Diagnostic Uses for Anti-g41

Another example of a technique in which the monoclonal antibody and the biological reactive fragments of the invention may be employed is in immunodiagnostic assays involving antigen-antibody reactions. The assays may be homogeneous or heterogeneous. In a homogeneous assay approach, the specimen may be biological fluid such as serum, urine, and the like or the specimen may be lysed and clarified to remove debris. The antibody, for example, can be used to measure the concentration of its cognate antigen in the serum of patients. The immunological reaction usually involves the specific antibody, a labeled analyte, and the sample of interest. The signal arising from the label is modified, directly or indirectly, upon the binding of the antibody to the labeled analyte. Both immunological reaction and detection of the extent thereof are carried out in a homogeneous solution. Immunochemical labels which may be employed include free radicals, fluorescent dyes, enzymes, bacteriophages, coenzymes, and so forth.

In a heterogenous assay approach, the reagents are usually the specimen, the specific antibody, and means for producing a detectable signal. The specimen is generally placed on a support, such as a plate or slide, and contacted with the antibody in a liquid phase. The support is then separated from the liquid phase and either the support phase or the liquid phase is examined for a detectable signal employing means for producing such signal. The signal is related to the presence of the analyte in the specimen. Means for producing a detectable signal includes the use of radioactive labels, fluorescent compounds, enzymes, and so forth. Exemplary heterogeneous immunoassays are the radioimmunoassay, immunofluorescence methods, enzyme-linked immunoassays, and the like.

For a more detailed discussion of the above immunoassay techniques, see "Enzyme-Immunoassay," by Edward T. Maggio, CRC Press, Inc., Boca Raton, Fla., 1980. See also, for example, U.S. Pat. Nos. 3,690,834; 3,791,932; 3,817,837; 3,850,578; 3,853,987; 3,867,517; 3,901,654; 3,935,074; 3,984,533; 3,966,345; and 4,098,876, which listing is not intended to be exhaustive. Methods for conjugating labels to antibodies and antibody fragments are well known in the art. Such methods may be found in U.S. Pat. Nos. 4,220,450; 4,235,869; 3,935,974; and 3,966,345. Another example of a technique in which the monoclonal antibody of the invention may be employed is immunoperoxidase labeling. (Sternberger, *Immunocytochemistry* (1979) pp. 104–169). Alternatively, the monoclonal antibody may be bound to a radioactive material or to a drug to form a radiopharmaceutical or pharmaceutical, respectively. (Carrasquillo, et al., *Cancer Treatment Reports* (1984) 68:317–328).

EXAMPLE 14

Therapeutic Uses of Fusion-Associated Epitope of Human Immunodeficiency Virus-1 (HIV-1)

With regard to active immunization, technology is now available for synthesis of vaccines derived from short amino acid sequences on the surface of a virus or other pathogen. Such small peptide sequences are capable of representing the immunogenic counterpart in the entire pathogen and of stimulating effective neutralizing antibody production. These synthetic vaccines are potentially "medically ideal" reagents, whose clinical applicability has now been studied for almost a decade. (Lerner, R. A., et al., *Hospital Practice* (1981) 16:55–62, December 1981, Vol. 16, No. 12, pp. 55–62).

The synthetic vaccine approach has been studied in SIV infection in macaques, on the basis of immunological studies with a set of SIV peptides chosen for hydrophilicity and conservation epitopes analogous to HIV gp120 and gp41. The immunogenic potential of a mixture of four of these epitopes (two from gp120 and two from gp41) was tested in macaques. One of the two SIV transmembrane synthetic peptide sequences, corresponding to the HIV-1 transmembrane gp41 amino acid sequence (amino acids 589–609) that contains the neutralizable fusion-associated epitope (amino acids 602–609) considered in this patent as an antigenic/immunogenic peptide of HIV-1, was one of the four subunit synthetic vaccine components utilized to successfully immunize the macaques against SIV challenge. (Shafferman, A., et al., Cold Spring Harbor Laboratory Symposium (September 1990) p. 90).

Other viral pathogens for which synthetic peptide vaccines have been successfully developed include foot-and-mouth disease of cattle (Bittle, J. L., et al., *Nature* (1982) 298:30; *Vaccine* 89, Cold Spring Harbor Laboratory Symposium (September 1989) p. 449) and hepatitis B virus in humans, for which a vaccine consists of a single viral protein, the surface antigen prepared by recombinant DNA technology. (Schild, G. C., et al., *Lancet* (1990) 335:1081).

The active immunization method, utilizing the HIV-1 fusion-associated epitope (peptide) can parallel that standardized for hepatitis B, wherein, for example, 20 micrograms of recombinant peptide is the inoculum per each of three inoculations (inoculum=1 ml) (IM-deltoid muscle), at time intervals of initial, one, and six months after the first dose (e.g., Engerix-B®, a hepatitis B recombinant peptide vaccine, manufactured by SmithKline Biologicals, Rixensart, Belgium, distributed by Smith Kline & French Laboratories, Division of SmithKline Beckman Corporation, Philadelphia, Pa. 19101).

Because it is not known whether the predominant route of initial HIV-1 infection in humans is by cell-associated virus or cell-free virus, it is important that any vaccine antibody response based on the gp41 fusion-associated epitope (GCSGKLIC) (SEQ NO:1) be able to block both infectious pathways. Again, it is significant, therefore, that Clone 3 Antibody, elicited by the native antigen identified in fine epitope mapping as in the octapeptide represented by the amino acid sequence GCSGKLIC (SEQ NO:1), can both prevent fusion of virus-infected cells and neutralize infectivity of free virus particles, as demonstrated by biological assays presented in Example 11 and Example 18, respectively.

Therefore, therapeutic measures capable of boosting the (decreasing) neutralizing antibody titer of individuals already infected with the human immunodeficiency virus-1 (HIV-1), eliciting high-titer neutralizing antibodies (i.e., active immunotherapy), or increasing (augmenting) neutralizing antibodies (i.e., passive immunotherapy) in individuals at risk would prove beneficial in preventing new infection or in controlling viral spread in vivo, (Robert-Guroff, et al., AIDS *Research and Human Retroviruses* (1988) 3:343–350), thereby preventing the disease progression to frank AIDS.

EXAMPLE 15

Prognostic Uses of Fusion-Associated Epitope of Human Immunodeficiecy Virus-1 (HIV-1) and Anti-gp41 (Clone 3 Antibody)

The peptide can be used as a prognostic tool to measure the concentration of the protecting antibody in the patient's serum. As mentioned previously, there is a correlation between level of protective antibody and the advancement of the disease. As protective antibody level decreases, the disease-state progresses.

Patient samples such as plasma, cerebral spinal fluid, secretions, or excretions may be collected for testing. The samples could then be tested in an in vitro ELISA for quantitating and detecting antibody against the peptide. Microtiter plates coated with the peptide could be used in the screening. The patient samples could be incubated on the peptide-coated plates in various dilutions for times sufficient to allow binding to occur. An anti-human antibody labeled either radioactively or enzymatically for subsequent detection could then be added to the wells. The simultaneous running of a standard curve with known antibody amounts would enable quantitation of the antibody in the patient samples.

Conversely, the human monoclonal antibody can be utilized to detect, monitor, and quantitate the concentration of the respective antigen/virus in the biological fluids listed above, or in a cell-associated state.

AIDS is caused by the retrovirus Human Immunodeficiency Virus-1 (HIV-1). HIV-1 infection is a chronic disease. The time between infection and the development of clinical AIDS probably averages 8 to 10 years. Laboratory tests for Human Immunodeficiency Virus-1 infection are commonly performed for two reasons.

First, diagnostic tests for the detection of the presence of HIV-1 antibodies can determine whether a person has been infected with the virus. Frequently the virus itself is not detected in patients who are seropositive for HIV-1 antibodies. In early stages of the disease most individuals who have been infected with HIV-1 do not develop clinical symptoms caused by the associated immunosuppression that gradually ensues and therefore most infected individuals are asymptomatic with regard to demonstrating signs of the illness.

Second, prognostic tests should be conducted to estimate the stage and activity of HIV-1 disease. Therefore, prognostic tests are important in identifying patients who might benefit from prophylactic therapy against HIV-1 disease progression.

A number of tests have been used to help estimate the rate of disease progression and the stage of disease. Monitoring these laboratory findings are helpful in patient clinical management. Quantitative tests include CD4+ (T-helper) lymphocytes counts, p24 antigen levels, and $beta_2$-microglobulin levels.

A decrease in average antibody titers (concentration) has been clinically observed in late stages of infection, particularly with regard to antibodies directed against the HIV-1 envelope epitopes and specifically against the TM gp41 region containing the amino acid sequence against which the herein described human monoclonal antibody (Clone 3 Antibody) is biologically reactive. (Shafferman, et al., *AIDS Research and Human Retroviruses* (1989) 5:33–39; Chiodi, et al., *J. Med. Virol.* (1987) 23:1–9; McPhee, et al., *FEBS Lett.* (1988) 233:393–396).

Specifically and significantly, it has been determined recently that a low IgG antibody titer (concentration) against a gp41 peptide (JB7) represented by amino acids CSGKLICTT (SEQ NO:12) (603–611, Wain-Hobson/Gnann numbering system) was found to be associated with a rapid disease progression to frank AIDS. (Broliden, et al., *AIDS* (1989 September) 3:577–582). The clinical correlation and the significant data are presented below:

Sera from children that had progressed to frank AIDS (symptomatic) contained almost no antibody reactivity against the indicated region of gp41, CSGKLICTT (SEQ NO:12). Only one out of seven sera from the children with frank AIDS showed antibody reactivity to CSGKLICTT (SEQ NO:12), compared with 12 out of 15 of the rest of the group infected with HIV-1, yet without symptoms of AIDS (asymptomatic).

This significant difference (P less than 0.025, chi square) regarding the concentration of antibodies against the gp41 peptide JB7, could not be seen in peptides representing other parts of gp41, i.e., JB2 and JB4.

The amino acid sequences (single letter abbreviations) are presented for gp41 peptide JB2 and gp41 peptide JB4, for comparison to the amino acid sequence for gp41 peptide JB7, a nine amino acid peptide which contains 7 of the 8 amino acids of the fusion-associated epitope. Additionally, the octapeptide amino acid sequence for the gp41 fusion-associated epitope, which contains 7 of the 9 amino acids of the JB7 peptide, is also provided below:

| | | |
|---|---|---|
| JB2 | $^{578}$IKQLQARILAVERYLKDQQLLGIWG$^{602}$ (Wain-Hobson/Gnann) | (Seq. No. 13) |
| JB4 | $^{599}$GIWGCSGKLICTTAVPWNAS$^{618}$ | (Seq. No. 14) |
| JB7 | $^{603}$CSGKLICTT$^{611}$ | (Seq. No. 12) |

Fusion-Associated Epitope$^{602}$GCSGKLIC$^{609}$ (Seq. No. 1)

However, anti-JB7 (antibody) response probably has no protective function against infection (i.e., absolute prevention of transmission of HIV-1) since the frequency of anti-JB7 (antibody) reactivity in the uninfected group (without HIV-1) was also low. The data indicated that only four sera from 19 of the uninfected children less than 6 months of age reacted with JB7, i.e., demonstrated the presence of anti-JB7 antibodies.

A similar difference of reactivity would probably be possible for identifying other significant (neutralizable) epitopes contained within gp41, with the corresponding (neutralizing) antibodies.

Fusion-Associated Epitope—The peptide can be synthesized according to the solid-phase method of Merrifield (1963) modified by Houghten (1985). For ELISA quantitation of human antibody directed against the fusion-associated epitope, microwell plates (NUNC Immunoplate 1) are coated at 4° C. overnight (or 3 hours at room temperature) with 1 microgram of peptide/microwell. The wells are washed three times with phosphate buffered saline (PBS) and are then incubated with 200 microliters of PBS containing 1% bovine serum albumin (BSA) per well at room temperature for 3 hours to block nonspecific protein binding sites. The wells are then emptied by aspiration, and washed three times with 300 microliters PBS containing 0.05% by volume polyoxyethylene (20) sorbitan monolaurate (e.g., Tween 20, produced by ICI Specialty Chemicals), then twice with 300 microliters of PBS alone. The wells are emptied, dried and the fusion-associated epitope/peptide coated plates are then stored with desiccant in a sealed bag at 4° C.

The test fluid (e.g., blood serum from a human patient or normal individual) is diluted with PBS containing 20% by volume normal goat serum, 1% by weight BSA and 0.05% by volume Tween 20 at dilutions of 1:50 (or 1:500), volume to volume.

In order to quantitate the human antibody in the test sera directed against the fusion-associated epitope, 100 microliters of the diluted sera are added to each well and allowed to react for 2 hours at 37° C. To construct a standard curve in order to calculate the concentrations in test sera of human antibodies directed against the fusion-associated epitope, a known concentration of affinity-chromatography purified Clone 3 Antibody (IgG1) is serially diluted and concomitantly reacted (100 microliters) in the peptide-coated wells. The wells are then washed five times with 0.05% by volume Tween 20 in PBS in order to remove Unbound antibodies. A solution of 100 microliters of horseradish peroxidase conjugated goat anti-human IgG at a dilution of 1:100 is used as a second antibody tracer to bind with the human antibody-antigen complex formed in positive wells After 2 hours at 37° C., the wells are washed three times with 0.05% by volume Tween in PBS, then incubated with 100 microliters of tetramethylbenzidine chromogen in dimethylsulfoxide (DMSO) with buffered hydrogen peroxide substrate for 30 minutes at room temperature. The reaction is stopped by the addition of 100 microliters of 1N sulfuric acid ($H_2SO_4$) and the optical density or absorbance of the solution determined at 490 nm, a colorimetric determination in the visible spectrum. Assays are performed in duplicate serum samples from normal individuals or from patients with diseases unrelated to HIV-1 infection used as negative controls. Absorbance readings greater than the cutoff value of $A_{490}=$ 0.12, (about 3 times the mean $A_{490}$ value of normal serum control), are recorded as positive.

A prognostic test kit for quantitation of human antibodies directed against the fusion-associated epitope of HIV-1 can be constructed. The test kit comprises a compartmented enclosure containing multiple 96-well plates coated prior to use with 1 microgram per well of the fusion-associated epitope/peptide of the present invention. The kit further comprises materials for enzyme detection in separate sealed containers consisting of: (1) normal human serum, as negative control; (2) quantitated affinity-chromatography purified Clone 3 Antibody (human monoclonal anti-fusion-associated epitope antibody directed against HIV-1 gp41), as positive control and for construction of a standard curve; (3) normal goat serum; (4) peroxidase labeled-goat antihuman IgG; (5) color change indicator consisting of tetramethylbenzidine chromogen in dimethylsulfoxide (DMSO) with buffered hydrogen peroxide substrate; and (6) 1N sulfuric acid ($H_2SO_4$). The procedure-described above is to be followed.

EXAMPLE 16

Development and Use of Synthetic Inhibitory Peptide

Since the amino acid sequence of the fusion-associated epitope is known, it is possible to synthetically develop a complementary peptide capable of binding to the epitope and thereby capable of blocking fusion. The development of a "synthetic inhibitory peptide" is facilitated in this instance since the tertiary structure of the epitope has been predicted through computer analysis. (Modrow, et al., *J. virol.*, (1987) 61:570–578; Navia, et al., V International Conference on AIDS (1989) Abstract No. M.C.O.23, p. 513; Debouck, et al., V International Conference on AIDS (1989), Abstract No. T.C.O.11, p. 517).

The amino acid sequence and tertiary structure of the epitope may be input as data into a computer program with 3-dimensional modeling capabilities. Several models of complementary peptides may then be generated. Peptide sequences consisting of the complementary peptides may then be synthesized and tested for fusion inhibition capacity, such as in a syncytium-forming assay. Those peptides found to inhibit fusion may then be produced on a larger scale for therapeutic purposes. Such peptides may be administered orally, intramuscularly, or intravenously.

Specifically, an example of the complementary synthetic inhibitory peptide on gp120 (amino acids 107–134, Myers) that has the biochemical property to form amphipathic helices with three charged amino acid residue contacts (shown below and underscored) and complementary hydrophobic residues on the gp41 (amino acids 584–611, Wain-Hobson/Gnann) and consequently inhibit the function of the fusion-associated epitope on gp41 (amino acid residues 602–609, Wain-Hobson/Gnann), would be, as deduced from the data presented by McPhee, et al., Cold Spring Harbor Symposium (1988), p. 17, and Modrow, S., id.:

$107_{D\text{-}I\text{-}I\text{-}S\text{-}L\text{-}W\text{-}\underline{D}\text{-}Q\text{-}S\text{-}L\text{-}}$
$\underline{K}\text{-}P\text{-}C\text{-}V\text{-}K\text{-}L\text{-}\underline{T}\text{-}P\text{-}L\text{-}C\text{-}V\text{-}S\text{-}L\text{-}K\text{-}C\text{-}T\text{-}D\text{-}L}134$    (Myers)    (SEQ NO: 15)

(single letter abbreviations representing amino acid residues 107–134, Myers).

The predicted three charged amino acid residue contacts (shown below and underscored) and the complementary hydrophobic amino acid residues that form part of the putative contact region between gp120 (amino acids 107–134, Myers) and gp41 (amino acids 584–611, Wain-Hobson/Gnann) and the relation to the fusion-associated epitope (shown below in bold type) on gp41 (amino acids 602–609, Wain-Hobson/Gnann), are represented in the comparison below.

*gp*120 105*H-E-D-I-I-S-L-W-D-Q-S-L-K-P-C-V-K-L-T-P-L-C-V-S-L-K-C-T-D-L*134
(Myers) (SEQ NO:16)

*gp*41 582*Q-A-R-I-L-A-V-E-R-Y-L-K-D-Q-Q-L-L-G-I-W-G-C-S-G-K-L-I-C-T-T*611
(Gnann) (SEQ NO:17)

Thus, with regard to the synthetic inhibitory peptide (neutralizing agent), the complementary synthetic inhibitory peptide sequence may be determined as presented above.

Additional data indicating that the antiviral synthetic inhibitory peptides against HIV-1 can be synthesized to mimic structures involved in the contact region between gp120 and gp41 are presented in McPhee, D. A., Vth International Conference on AIDS, Montreal, Canada, June 1989, Abstract T.C.O. 35, Putative Interaction Site Between HIV gp120 and gp41: Antiviral Action of Synthetic Peptides, p. 521.

Synthetic peptides of 8 to 25 amino acid residues were tested by McPhee (at 50–100 micrograms/ml) for their ability to inhibit HIV replication in vitro. A region in gp120 (amino acids 99–119) was identified that inhibited virus replication as demonstrated by lack of increase in reverse transcriptase (RT) activity and delayed syncytial formation. (McPhee, id.).

Specifically, of the peptides tested and reported by McPhee, gp120 (105–117) had marked antiviral activity (99% inhibition of RT activity after 11 days in culture) (FIG. 2A). (McPhee, D. A., *Vaccines* 89, Putative Contact Region Between HIV Envelope Proteins gp120 and gp41: Antiviral Action of Synthetic Peptide Analogs, September 1989, pp. 185–189.)

It should also be noted, however, in the reported preliminary experiment that the 25-residue synthetic peptide gp120 (105–129) had only 50% inhibition of RT activity after 11 days in culture. (McPhee, id., p. 185).

This synthetic inhibitory peptide (105–129) tested by McPhee did not span entirely the complementary hydrophobic and counterpart gp41 region that contains the fusion-associated epitope, as does the synthetic inhibitory peptide gp120 (107–134) described and represented above by the Applicant.

EXAMPLE 17

Development and Use of Anti-Idiotypic Antibodies

The human monoclonal antibody Anti-gp41 may be injected as an immunogen into another species, such as mice, in order to raise anti-idiotypic antibodies to the Anti-gp41. Monoclonal anti-idiotypes could also be developed. Anti-idiotypes could be screened for using available assay techniques effecting a competition between the labeled peptide and the potential anti-idiotypes. Those anti-idiotypes capable of displacing the peptide in assay could then be used in place of the peptide for purposes of immunization or diagnosis.

EXAMPLE 18

Neutralizatiom of HIV-1 (SF2) Infectivity by Human Monoclonal Antibody Directed Against gp41

The free virus neutralization assay is conducted as follows: Aliquots of seronegative sera or affinity column (Protein G) purified human monoclonal anti-gp41 antibody (Clone 3 Antibody) (dilutions 1:10 and 1:100) are incubated with HIV-1 (SF2) for 1 hour at 37° C. The virus and antibody sample is then reacted for 3 hours at 37° C. with PHA stimulated (3 days) peripheral blood mononuclear cells (PBMC) obtained from normal donors. The supernatant is removed and replaced by growth media after the 3 hour incubation. On day 8 postinfection, the supernatant media (quadruplicates) are assayed for reverse transcriptase (RT) activity.

A human monoclonal antibody (Clone 3 Antibody) concentration of 100 micrograms/ml produced a 96% inhibition of free virus (SF2) infectivity of human mononuclear cells as demonstrated by lack of increase in reverse transcriptase (RT) activity when cell-free supernatant fluids were analyzed on day 8 postinfection (Table 5).

TABLE FIVE

Neutralization of HIV-1 (SF2) Infectivity By Human Monoclonal Antibody (Clone 3 Antibody) Directed Against gp41

| HIV-1 | Reverse Transcriptase (RT) Activity ($\times 10^3$ cpm/ml) | | |
|---|---|---|---|
| | Normal Patient Serum | Human Monoclonal Antibody | |
| Virus Strain | (control) | (10 μg/ml) | (100 μg/ml) |
| SF2 | 60.0 | 12.0 | 2.5 |
| Percent Inhibition | — | 80% | 96% |

Reference: C. Cheng-Mayer, et al., Proceedings of the National Academy of Sciences, USA, Volume 85, pp. 2815–2819, April 1988, Identification of Human Immunodeficiency Virus Subtypes with Distinct Patterns of Sensitivity to Serum Neutralization.

EXAMPLE 19

Immunofluorescence Assay by Flow Cytometry

The indirect immunofluorescence staining procedure was performed as described below.

Aliquots of live Sup-T1 cells ($10^6$ in 50 microliters PBS with 0.1% BSA and 0.02% sodium azide), either HTLV-IIIB.9 infected or uninfected, were incubated in parallel procedures with 5 microliters of human monoclonal antibody (Clone 3 Antibody) supernatant for 30 minutes at 4° C. The cells were washed and resuspended in 25 microliters of a 1:40 dilution of affinity-purified fluorescein isothiocyanate (FITC)-conjugated $(Fab')_2$ goat anti-human IgG (gamma chain specific) (Tago, Burlingame, Calif.) for an additional 30 minutes at 4° C. After incubation, the cells were washed repeatedly, fixed in 4% paraformaldehyde, and then ten thousand stained cells were analyzed by flow cytometry using a Becton Dickinson FACS analyzer interfaced to a BD Consort 30 (Becton Dickinson, Mountain View, Calif.). Cells uninfected by HTLV-IIIB.9 served as a negative control.

The fluorescence profiles of the binding of human monoclonal antibody (Clone 3 Antibody) to [A] HTLV-IIIB.9 infected Sup-T1 cells (mean relative fluorescence intensity=127) and [B]uninfected Sup-T1 cells (mean relative fluorescence intensity=7) as measured by cytofluorographic analysis, are represented in FIG. 9, wherein relative log green fluorescence intensity (abscissa) is plotted versus relative cell number (ordinate).

The human monoclonal antibody (Clone 3 Antibody)

reacted in indirect immunofluorescence assays with a significant proportion of viable HIV-infected cells suggesting that the determinant (epitope) recognized by the antibody is expressed on the surface of HIV-infected cells (and not on uninfected cells) and may be an exposed component of the envelope of HIV.

Therefore, the HIV-specific human monoclonal antibody (Clone 3 Antibody) directed against the transmembrane (TM) envelope gp41 fusion-associated octapeptide epitope with the amino acid sequence GCSGKLIC (SEQ NO:1) (602–609$^{Wain-Hobson}$) demonstrated in cytofluorographic analysis, reactivity to the native TM envelope glycoprotein gp41.

These data suggest that the octapeptide with the amino acid sequence GCSGKLIC (SEQ NO:1) ($602–609^{Wain-Hobson}$) represents a native antigenic determinant (epitope) of HIV-1 TM envelope glycoprotein gp41 which is expressed on the surface of HIV-infected cells and also elicits a postinfection immune response with the production of neutralizing antibody, e.g., Clone 3 Antibody.

Although preferred embodiments of the invention have been described in the foregoing Detailed Description, it will be understood that the invention is not limited to the embodiments disclosed, but is capable of numerous rearrangements and modifications without departing from the spirit of the invention. The present invention is therefore intended to encompass such rearrangements and modifications as fall within the scope and spirit of the invention.

I claim:

1. A hybridoma having all of the identifying characteristics of the hybridoma designated Clone 3 having A.T.C.C. Accession No. CRL 10198, said hybridoma producing a human monoclonal antibody which immunologically binds to the transmembrane glycoprotein, gp41, of Human Immunodeficiency Virus Type 1.

2. A human monoclonal antibody produced by the hybridoma of claim 1.

* * * * *

UNITED STATES PATENT AND TRADEMARK OFFICE
CERTIFICATE OF CORRECTION

PATENT NO. : 5,459,060
DATED : October 17, 1995
INVENTOR(S) : Joseph P. Cotropia It is certified that error appears in the above-indentified patent and that said Letters Patent is hereby corrected as shown below:

Column 11, lines 56-57, A paragraph break should appear between "Human Monoclonal Antibody Screening By Enzyme-Linked Immunosorbent Assays (ELISA)" and "Supernatants from";

Column 15, line 25, delete "Epitome" and insert --Epitope--;

Column 15, line 64, delete "ely" and insert --Gly--; and

Column 15, line 64, delete "(8-met)" and insert --(8-mer)--.

Signed and Sealed this

Sixteenth Day of April, 1996

Attest:

BRUCE LEHMAN

Attesting Officer

Commissioner of Patents and Trademarks